United States Patent
Hurley

(10) Patent No.: US 11,470,921 B2
(45) Date of Patent: Oct. 18, 2022

(54) ADJUSTABLE CLOSURE DEVICES WITH HANDLE AND LOCKING MECHANISMS

(71) Applicant: Garrett Ray Hurley, San Francisco, CA (US)

(72) Inventor: Garrett Ray Hurley, San Francisco, CA (US)

(*) Notice: Subject to any disclaimer, the term of this patent is extended or adjusted under 35 U.S.C. 154(b) by 0 days.

(21) Appl. No.: 17/615,789

(22) PCT Filed: Jun. 4, 2020

(86) PCT No.: PCT/US2020/036140
§ 371 (c)(1),
(2) Date: Dec. 1, 2021

(87) PCT Pub. No.: WO2020/247645
PCT Pub. Date: Dec. 10, 2020

(65) Prior Publication Data
US 2022/0202141 A1 Jun. 30, 2022

Related U.S. Application Data

(60) Provisional application No. 62/937,808, filed on Nov. 20, 2019, provisional application No. 62/857,320, filed on Jun. 5, 2019.

(51) Int. Cl.
*A44B 11/12* (2006.01)
(52) U.S. Cl.
CPC .................. *A44B 11/125* (2013.01)
(58) Field of Classification Search
CPC ...... A44B 11/125; A44B 11/12; Y10T 24/318
See application file for complete search history.

(56) References Cited

U.S. PATENT DOCUMENTS

| | | | |
|---|---|---|---|
| 48,121 A * | 6/1865 | Warner | A44B 11/12 24/191 |
| 843,979 A | 2/1907 | Wantz | |
| 956,328 A | 4/1910 | Forshee | |
| 1,107,934 A | 8/1914 | Hagan | |
| 2,191,228 A * | 2/1940 | Dowd | A44B 11/125 24/170 |
| 2,604,098 A | 7/1952 | Kranc | |
| 2,699,918 A | 1/1955 | Bush | |
| 2,754,825 A | 7/1956 | Richmond | |

(Continued)

*Primary Examiner* — Robert Sandy
(74) *Attorney, Agent, or Firm* — Gordon & Jacobson, P.C.

(57) ABSTRACT

Embodiments of the invention are directed to adjustable closure devices. One embodiment has a strap, a connector attached to a strap end, a chafe mounted on the strap behind the connector, and a hinged handle on the chafe. The chafe has a two outer bars and a central bar, these bars defining strap through-paths. The strap end-region has path segments arranged, directionally from the strap's central region toward the strap end at the chafe, or, in embodiments that configure the strap as a pulley, at the connector. An adjustable length region of the strap spans between the chafe and the connector. An elevatable handle configuration allows a user to pull the chafe to which it is connected along the strap, away from connector. As the chafe moves along the strap, the strap can transition between a large circumference configuration and small circumference. Some embodiments have a strap friction-locking mechanism associated with the handle and the chafe.

24 Claims, 20 Drawing Sheets

(56) References Cited

U.S. PATENT DOCUMENTS

| | | |
|---|---|---|
| 2,889,136 A | 6/1959 | Prete, Jr. |
| 2,969,221 A | 1/1961 | Harmes |
| 3,175,806 A | 3/1965 | Prete, Jr. |
| 3,180,623 A | 4/1965 | Huber |
| 3,279,760 A | 10/1966 | Bathum, Jr. |
| 3,315,913 A | 4/1967 | Grieten |
| 3,667,698 A | 6/1972 | Fisher |
| 3,749,366 A | 7/1973 | Brucker |
| 3,825,979 A | 7/1974 | Jakob |
| 4,044,400 A | 8/1977 | Lewicki |
| 4,154,427 A | 5/1979 | Hofmann |
| 4,155,537 A | 5/1979 | Bronson |
| 4,199,182 A | 4/1980 | Sunesson |
| 4,278,002 A | 7/1981 | Siminoff |
| 4,345,726 A | 8/1982 | Noda |
| 4,436,254 A | 3/1984 | Normann |
| 4,507,829 A | 4/1985 | Looker |
| 4,542,883 A | 9/1985 | Rutzki |
| 4,612,686 A | 9/1986 | Bowers |
| 4,703,917 A | 11/1987 | Tomlinson |
| 4,738,410 A | 4/1988 | Yamaguchi |
| 4,823,443 A | 4/1989 | Waters |
| 5,203,541 A | 4/1993 | Nix |
| 5,271,606 A | 12/1993 | Kaemper |
| 5,295,664 A | 3/1994 | Kaemper |
| 5,325,613 A | 7/1994 | Sussmann |
| 5,426,827 A | 6/1995 | Tracy |
| 5,495,683 A | 3/1996 | Miotto |
| 5,542,798 A | 8/1996 | Rawdon |
| 5,606,779 A | 3/1997 | Lu |
| 5,720,084 A | 2/1998 | Chen |
| 5,800,105 A | 9/1998 | Stump |
| 5,904,341 A | 5/1999 | Norrby |
| 5,909,850 A | 6/1999 | Cavasin |
| 6,003,578 A | 12/1999 | Chang |
| 6,007,053 A | 12/1999 | Huang |
| 6,095,450 A | 8/2000 | Jang |
| 6,547,218 B2 | 4/2003 | Landy |
| 6,654,987 B1 | 12/2003 | Wu |
| 6,772,485 B2 * | 8/2004 | Alpert .......... A45C 13/30 190/102 |
| 6,880,810 B1 | 4/2005 | Hu |
| 7,207,089 B2 | 4/2007 | Hanson |
| 7,503,546 B1 | 3/2009 | Seager |
| 7,503,736 B1 | 3/2009 | Chen |
| 7,510,168 B1 | 3/2009 | Lin |
| 7,644,906 B2 | 1/2010 | Rodrigue |
| 7,877,845 B2 | 2/2011 | Signori |
| 8,099,836 B2 | 1/2012 | Breeden |
| 8,109,015 B2 | 2/2012 | Signori |
| 8,277,401 B2 | 10/2012 | Hammerslag |
| 8,434,200 B2 | 5/2013 | Chen |
| 8,516,662 B2 | 8/2013 | Goodman |
| 8,794,378 B2 | 8/2014 | Wolner |
| 8,904,672 B1 | 12/2014 | Johnson |
| 8,919,293 B2 | 12/2014 | Cromwell |
| 8,967,332 B2 | 3/2015 | Wolner |
| 9,138,030 B2 | 9/2015 | Soderberg |
| 9,179,729 B2 | 11/2015 | Cotterman |
| 9,185,942 B2 | 11/2015 | Rowland |
| 9,277,776 B2 | 3/2016 | Laatz |
| 9,285,776 B1 | 3/2016 | Custer |
| 9,296,534 B2 | 3/2016 | Gerhardt |
| 9,351,539 B2 | 5/2016 | Briggs |
| 9,572,405 B2 | 2/2017 | Saris |
| 9,597,786 B2 | 3/2017 | Romo |
| 9,635,906 B2 | 5/2017 | Midorikawa |
| 9,656,591 B1 | 5/2017 | Dumenigo |
| 9,657,485 B2 | 5/2017 | Meyers |
| 9,706,814 B2 | 7/2017 | Converse |
| 9,725,029 B2 | 8/2017 | Chou |
| 9,770,069 B2 | 9/2017 | Munns |
| 9,770,070 B2 | 9/2017 | Cotterman |
| 9,788,613 B2 | 10/2017 | Steffenhagen |
| 9,855,055 B2 | 1/2018 | Kosiorek |
| 9,867,430 B2 | 1/2018 | Hammerslag |
| 9,918,865 B2 | 3/2018 | Nickel |
| 9,956,094 B2 | 5/2018 | Mahon |
| 9,968,473 B2 | 5/2018 | Mason |
| 9,993,048 B2 | 6/2018 | Casebolt |
| 10,016,203 B2 | 7/2018 | Esposito |
| 10,070,695 B2 | 9/2018 | Burns |
| 10,076,160 B2 | 9/2018 | Burns |
| 10,077,570 B2 | 9/2018 | Underwood |
| 10,085,502 B1 | 10/2018 | Trepanier |
| 10,088,016 B2 | 10/2018 | Bujold |
| 10,160,419 B2 | 12/2018 | Wedeking |
| 10,227,030 B2 | 3/2019 | Kingery |
| 10,251,451 B2 | 4/2019 | Converse |
| 10,264,852 B2 | 4/2019 | Kim |
| 10,266,364 B2 | 4/2019 | Hitsman |
| 10,308,163 B2 | 6/2019 | Helline |
| 10,363,046 B2 | 7/2019 | Hopman |
| 10,413,019 B2 | 9/2019 | Soderberg |
| 10,414,323 B2 | 9/2019 | Willodson |
| 10,492,568 B2 | 12/2019 | Burns |
| 10,543,630 B2 | 1/2020 | Hipwood |
| 10,558,052 B2 | 2/2020 | Chang |
| 10,575,591 B2 | 3/2020 | Schum |
| 10,575,592 B1 | 3/2020 | Jones |
| 10,576,015 B2 | 3/2020 | Wang |
| 2003/0097736 A1 * | 5/2003 | Blankenship .......... A63B 57/00 24/302 |
| 2003/0145434 A1 | 8/2003 | Lin |
| 2004/0155230 A1 | 8/2004 | Fortin |
| 2005/0087115 A1 | 4/2005 | Martin |
| 2005/0177984 A1 | 8/2005 | Huang |
| 2005/0267518 A1 | 12/2005 | Wright |
| 2006/0156517 A1 | 7/2006 | Hammerslag |
| 2007/0101615 A1 | 5/2007 | Munns |
| 2008/0104811 A1 | 5/2008 | Burrows |
| 2008/0184451 A1 | 8/2008 | Lemke |
| 2008/0216213 A1 | 9/2008 | Lin |
| 2008/0216291 A1 | 9/2008 | Lin |
| 2008/0232922 A1 | 9/2008 | Chang |
| 2009/0271976 A1 | 11/2009 | Huang |
| 2009/0283729 A1 | 11/2009 | Carlson |
| 2009/0300889 A1 | 12/2009 | Shiue |
| 2010/0071174 A1 | 3/2010 | Adcock |
| 2010/0137900 A1 | 6/2010 | Chao |
| 2010/0244543 A1 | 9/2010 | Fine |
| 2010/0293765 A1 | 11/2010 | Huang |
| 2012/0138883 A1 | 6/2012 | Gallagher |
| 2012/0205601 A1 | 8/2012 | Joubert |
| 2012/0227223 A1 | 9/2012 | Knox |
| 2013/0025100 A1 | 1/2013 | Ha |
| 2013/0161365 A1 | 6/2013 | Shih |
| 2013/0269628 A1 | 10/2013 | Holt, Jr. |
| 2013/0318827 A1 | 12/2013 | Ringholz |
| 2013/0326847 A1 | 12/2013 | Zheng |
| 2013/0340292 A1 | 12/2013 | Cook |
| 2014/0061556 A1 | 3/2014 | Knox |
| 2014/0221889 A1 | 8/2014 | Burns |
| 2014/0338161 A1 | 11/2014 | Armour |
| 2015/0038889 A1 | 2/2015 | Mason |
| 2015/0040359 A1 | 2/2015 | Brown |
| 2015/0051638 A1 | 2/2015 | Dickinson |
| 2015/0053806 A1 | 2/2015 | Geisel |
| 2015/0121669 A1 | 5/2015 | Jungkind |
| 2015/0158615 A1 | 6/2015 | Downs |
| 2015/0230560 A1 | 8/2015 | Chen |
| 2015/0257767 A1 | 9/2015 | Henderson |
| 2015/0289609 A1 | 10/2015 | Gittens |
| 2015/0359542 A1 | 12/2015 | Steinbaugh |
| 2016/0199206 A1 | 7/2016 | Lim |
| 2016/0206937 A1 | 7/2016 | Hanson |
| 2017/0100131 A1 | 4/2017 | Olbu |
| 2017/0295888 A1 | 10/2017 | Chen |
| 2017/0355298 A1 | 12/2017 | Cahall |
| 2018/0154862 A1 | 6/2018 | Wedeking |
| 2018/0334075 A1 | 11/2018 | Frank |
| 2019/0150569 A1 | 5/2019 | Chen |
| 2019/0216176 A1 | 7/2019 | Converse |

(56) References Cited

U.S. PATENT DOCUMENTS

\* cited by examiner

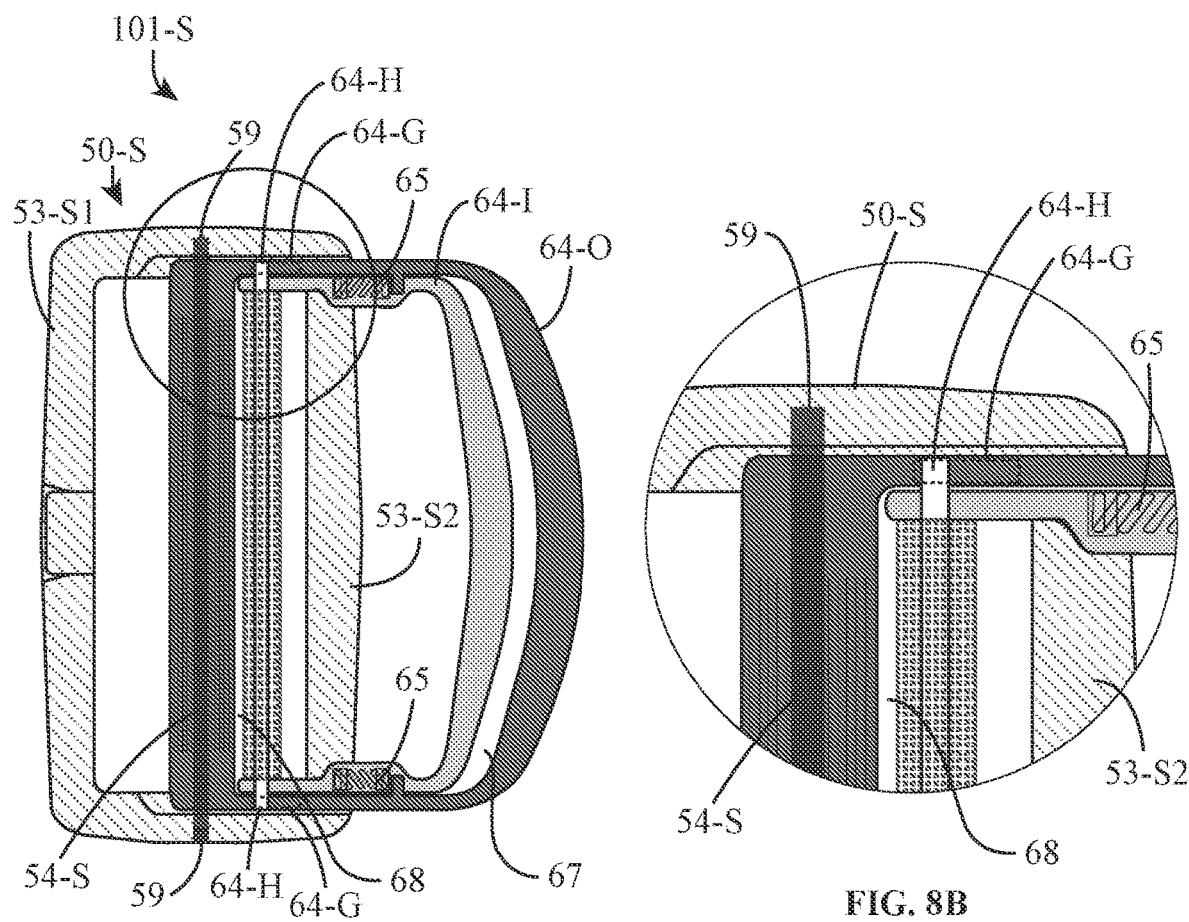
FIG. 8A
FIG. 8B
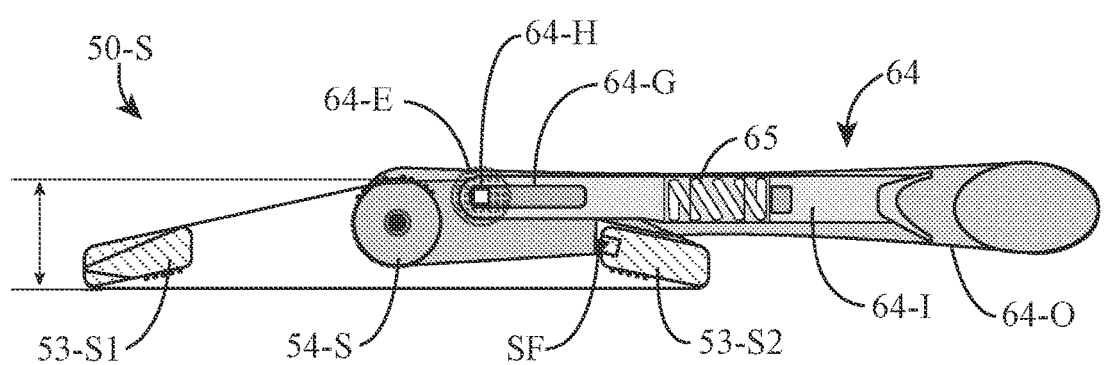
FIG. 8C

ADJUSTABLE CLOSURE DEVICES WITH HANDLE AND LOCKING MECHANISMS

CROSS REFERENCE

This application is the National Stage of International Patent Application No. PCT/US2020/036140 filed on Jun. 4, 2020, which claims priority to U.S. Provisional Patent Application No. 62/857,320, as filed on Jun. 5, 2019 and to U.S. Provisional Patent Application No. 62/937,808, as filed on Nov. 20, 2019.

TECHNICAL FIELD

This application is directed to adjustable closure devices that may be applied to articles, and particularly to wearable articles.

BACKGROUND

Adjustable closure devices that are adjustable by way of tensioning lines, such as cable-form or strap form lines have widespread use, including use as wearable article.

SUMMARY OF THE TECHNOLOGY

In one embodiment an adjustable closure device, one with unilateral strap length adjustability, the device includes (a) a strap that includes a first end-region, and a central region; (b) a connectable connector, wherein the connector is attached to a terminus of the strap end-region, and wherein the connector includes a first strap pivot bar and a second pivot bar, internal to the first strap pivot bar; and a chafe mounted at the end of at the strap end-region. The chafe includes three parallel bars, a first outer bar, a central bar, and a second outer bar, wherein the first outer bar is proximate the first end-region of the strap, the second outer bar is proximate the central-region of the strap, and wherein a first strap pass-through gap is disposed between the central bar and the first outer bar, and a second strap pass-through gap is disposed between the central bar and second outer bar. In this embodiment, the strap end-region has a strap path that includes segments arranged, directionally from the strap's central region and toward the strap terminus, to (a) pass through the first chafe gap, (b) pass by the central chafe bar, (c) pass through the second chafe gap, (d) pass toward the connector, to loop around the second pivot bar and reversing direction, (e) returning toward the chafe to pass around the central bar of the chafe and reversing direction, and finally (f) returning toward the connector, to loop around the first pivot bar of the connector and there to terminate. In some embodiments, an adjustable length region of the strap has an adjustable span between the chafe and the connector; and a handle connected to the chafe, wherein the handle is ergonomically configured to allow a user to pull the chafe along the strap, away from the connector. In these embodiments, when the chafe is allowed to move with respect to the strap and wherein the strap can move between two configurations, wherein, by comparison, a first configuration has a large strap circumference and a second configuration has a small strap circumference.

In some of these embodiments, the strap path includes a pulley arrangement in which the strap reverses direction twice, thereby providing mechanical advantage upon pulling the chafe with respect to the strap, wherein the force required to shorten the adjustable length region of strap is less than that which would be required absent the pulley arrangement to move the device from the first configuration to the second configuration. In some of these embodiments, the mechanical advantage is about 2:1.

In some of these embodiments, the adjustable closure device, the central region of the strap is continuous with a second end region of the strap.

In some of these embodiments the connector is mateable with a second connector attached to a second terminus of the strap. Further, in some of these embodiments, the strap attached to the second terminus of the strap includes a second adjustable length region.

In some of these embodiments, the second connector is attached to a separate article. And in some embodiments, the central region of the strap is attached to an article.

In some of these embodiments of an adjustable closure device, the chafe includes a connector-side and a central-side, and wherein the handle is connected to the chafe at a mounting site proximate the central bar of the chafe, and wherein the mounting site has a hinge supporting the handle. In some particular embodiments, the handle of the chafe can rotate at the hinge between a down position and an elevated position, wherein the elevated position elevates the handle on the central side of the chafe. And in some particular embodiments, the chafe has a handle-down retention mechanism.

In some of these embodiments of an adjustable closure device, the chafe includes a strap friction-locking mechanism, which, when in a locked position, disallows strap slippage through the chafe, and which, when in an unlocked position, allows strap slippage through the chafe. In particular of these embodiments, the adjustable length region of the strap includes two overlapping sections of the strap, a first section proximate the central region of the strap and a second section proximate the connector, and wherein the strap friction-based locking mechanism is positioned to engage on the adjustable length region of the strap.

In some embodiments of an adjustable closure device, the strap friction-locking mechanism includes a configuration wherein a base of the handle and the central bar of the chafe are integrated together, and wherein the central bar is configured as a one-sided cam. In particular of these embodiments, the one-sided cam is rotated such that the cam has a maximal peak height over the side bars of the chafe, the chafe is in a locked position, and wherein when the one-sided cam is rotated such that the one side cam does not rise over a minimal circumference of the central bar, the chafe is in an unlocked position.

In some embodiments of an adjustable closure device, the strap friction-locking mechanism includes a configuration wherein a base of the handle and the central bar of the chafe are integrated together, and wherein the central bar is configured as a two-sided cam. In particular of these embodiments, when the two-sided cam is rotated such that the cam has a maximal peak height over the side bars of the chafe, the chafe is in a locked position, and wherein when the two-sided cam is rotated such that the two-sided cam does not rise over a minimal circumference of the central bar, the chafe is in an unlocked position.

In some embodiments of an adjustable closure device, the chafe handle includes two parts, an outer handle and an inner handle, wherein the inner handle is nested within the outer handle and connected by a hinge thereto, wherein the inner handle and the outer handle are adjustable with respect to each other such that the two handle parts can be spaced apart or aligned together, wherein when the two handle parts are spaced apart, the chafe is in a locked position, and when two handle parts are aligned together, the chafe is in an unlocked position.

Some of these embodiments further include a spring that when in an uncompressed state, maintains the first and second handle parts in the spaced apart configuration such that the chafe is in the unlocked position, and when the spring is in a compressed state, the first and second handle parts are aligned together, and the chafe is a locked configuration. In brief, in embodiments of an adjustable closure device having a two-part handle with a spring controlled locking mechanism, the two-part handle has a spring-based bias that defaults the chafe into a locked configuration and remains in the locked configuration until a manually directed force moves the mechanism into a second, unlocked, configuration which diminishes the friction between the chafe and the strap, thereby allowing ease in adjusting an adjustable region of the strap, thereby allowing ease in moving the strap back and forth between a small circumference and large circumference configuration.

In some embodiments of an adjustable closure device, the handle includes a cam-configured base that is proximate the central bar of the chafe but separated therefrom by a strap gap through which the strap path passes. And in some particular embodiments, when the handle is in a down position the cam aspect of the base minimizes the strap gap, forming a locked configuration, and wherein when the handle is in an elevated position, the cam aspect of the base maximizes the strap gap, forming an unlocked configuration.

In a second embodiment of an adjustable closure device, one with bilateral strap adjustability, the device includes a strap having a first end-region, a central region, and a second end-region; two mutually connectable connectors, a first connector and second connector, wherein each connector is attached is to a terminus of one of the strap end-regions wherein each connector includes a first strap pivot bar and second pivot bar, internal to the first strap pivot bar; and two chafes, one mounted at the end of at each strap end-region. Each chafe includes three parallel bars, a first outer bar, a central bar, and a second outer bar, wherein the first outer bar is proximate the first end-region of the strap, the second outer bar is proximate the central-region of the strap, and wherein a first strap pass-through gap is disposed between the central bar and the first outer bar, and a second strap pass-through gap is disposed between the central bar and second outer bar. Further, each strap end-region includes a strap path having segments arranged, directionally from the strap's central region and toward the strap terminus, to (a) pass through the first chafe gap, (b) pass by the central chafe bar, (c) pass through the second chafe gap, (d) pass toward the connector, to loop around the second pivot bar and reversing direction, (e) returning toward the chafe to pass around the central bar of the chafe and reversing direction, and finally (f) returning toward the connector, to loop around the first pivot bar of the connector and terminate thereto. An adjustable length region of the strap includes an adjustable span between the each of the two chafes, the two chafes being connected by the connectors; and a handle connected to each chafe, wherein the handle is ergonomically configured to allow a user to pull each chafe along the strap, away from the first connector. Each chafe is allowed to move with respect to the strap and wherein the strap can move between two configurations, wherein, by comparison, a first configuration having a large strap circumference and a second configuration having a small strap circumference. In some of these embodiments of the adjustable closure device, the strap path includes a pulley arrangement in which the strap reverses direction twice, thereby providing a 2:1 mechanical advantage upon pulling the chafes with respect to the strap, in terms of the force required to shorten the adjustable length region, thereby moving from the first configuration to the second configuration. In particular of these embodiments the mechanical advantage is about 2:1.

BRIEF DESCRIPTION OF THE FIGURES

FIG. 1A is a top perspective view of an embodiment of an adjustable closure device in a large circumference configuration.

FIG. 1B is a top perspective view of an embodiment of an adjustable closure device in a small circumference configuration.

FIG. 2A is a perspective view of an embodiment of an adjustable closure device, showing, in particular, the two ends of a strap, the straps connected by mutually connectable elements, and a chafe disposed on both straps into which the strap ends terminate.

FIG. 2B is a side view of the embodiment of the adjustable closure device of FIG. 2A.

FIG. 2C is a detailed view of a portion of FIG. 2B.

FIG. 3A is a face view of an adjustable closure device with bilateral strap adjustability, showing in particular, the path of a strap through the connectors and chafes within the device.

FIG. 3B is a side view of an adjustable closure device with bilateral strap adjustability, showing in particular, the path of a strap through the connectors and chafes within the device.

FIG. 3C is a detailed view of a portion of FIG. 3B.

FIG. 4A is a face view of an adjustable closure device with unilateral adjustability, showing in particular, the path of a strap through the connectors and chafes within the device.

FIG. 4B is a side view of an adjustable closure device with unilateral adjustability, showing in particular, the path of a strap through the connectors and chafes within the device.

FIG. 4C is a detailed view of a portion of FIG. 4B.

FIG. 5A is a face view of a chafe and hinged handle.

FIG. 5B is a side view of a chafe and hinged handle, with the handle in a down position.

FIG. 5C is a side view of a chafe and hinged handle, with the handle in an elevated position.

FIG. 5D is a side view of a chafe and hinged handle, with the handle in a down position, and further showing the path of a strap through the chafe.

FIG. 5E is a side view of a chafe and hinged handle, with the handle in an elevated position, and further showing the path of a strap through the chafe.

FIG. 6A is a face view of a chafe and handle having an integrated one-sided cam that acts as friction-based strap lock.

FIG. 6B is a side view of a chafe and handle having an integrated one-sided cam that acts as friction-based strap lock, the handle in a down position.

FIG. 6C is a side view of a chafe and handle having an integrated one-sided cam that acts as friction-based strap lock, the handle in an elevated position.

FIG. 6D is a side view of a chafe and handle having an integrated one-sided cam that acts as friction-based strap lock, the handle in a down position, and further showing the path of a strap through the chafe.

FIG. 6E is a side view of a chafe and handle having an integrated one-sided cam that acts as friction-based strap lock, the handle in an elevated position, and further showing the path of a strap through the chafe.

FIG. 7A is a face view of an embodiment of an adjustable closure device with a chafe having a central bar configured as a two sided cam that acts as friction-based strap lock.

FIG. 7B is a side view of an embodiment of an adjustable closure device with a chafe having a central bar configured as a two sided cam that acts as friction-based strap lock, with the handle of the chafe in a down position.

FIG. 7C is a side view of an embodiment of an adjustable closure device with a chafe having a central bar configured as a two sided cam that acts as friction-based strap lock, with the handle of the chafe in an elevated position.

FIG. 7D is a side view of an embodiment of an adjustable closure device with a chafe having a central bar configured as a two sided cam that acts as friction-based strap lock, with the handle of the chafe in a down position, and further showing the path of a strap through the chafe.

FIG. 7E is a side view of an embodiment of an adjustable closure device with a chafe having a central bar configured as a two sided cam that acts as friction-based strap lock, with the handle of the chafe in an elevated position, and further showing the path of a strap through the chafe.

FIG. 7F is a side view of an embodiment of an adjustable closure device with a chafe having a central bar configured as a two sided cam that acts as friction-based strap lock, and with an implement attached to the bottom side of the handle.

FIGS. 8A-8G show views of an embodiment of an adjustable closure device with a two-part handle that has a spring based mechanism that acts as friction-based strap lock. FIG. 8A is a face view of an embodiment of an adjustable closure device with a two-part handle that has a spring based mechanism that acts as friction-based strap lock.

FIG. 8B is a detailed view of the spring based mechanism shown in FIG. 8A.

FIG. 8C is a side view of an embodiment of an adjustable closure device with a two-part handle that has a spring based mechanism that acts as friction-based strap lock with the two-part handle of the chafe in a down position.

FIG. 8D is a face view of an embodiment of an adjustable closure device with a two-part handle that has a spring based mechanism that acts as friction-based strap lock with the two-parts of the handle in a separated position, the spring in an uncompressed configuration.

FIG. 8E is a face view of an embodiment of an adjustable closure device with a two-part handle that has a spring based mechanism that acts as friction-based strap lock with the two-parts of the handle in a closed position, the spring in a compressed configuration.

FIG. 8F is a side view of an embodiment of an adjustable closure device with a two-part handle that has a spring based mechanism that acts as friction-based strap lock with the two-part of the handle in down position, the two parts of the handle in a separated position, and further showing the path of the strap through the connector and the chafe.

FIG. 8G is a side view of an embodiment of an adjustable closure device with a two-part handle that has a spring based mechanism that acts as friction-based strap lock with the two-part of the handle in an elevated position, the two parts of the handle in a compressed position, and further showing the path of the strap through the connector and the chafe.

FIG. 9A is a face view of a chafe and hinged handle of an embodiment of an adjustable closure device having a handle with an integrated cam positioned proximate the central bar of a chafe, the cam configured to act as friction-based strap lock.

FIG. 9B is a side view of a chafe and hinged handle of FIG. 9A, with the handle in a down position.

FIG. 9C is a side view of a chafe and hinged handle FIG. 9A, with the handle in an elevated position.

FIG. 9D is a side view of a chafe and hinged handle with the handle in a down position as in FIG. 9B, but further showing the path of a strap through the chafe.

FIG. 9E is a side view of a chafe and hinged handle with the handle in an elevated position as in FIG. 9C, but further showing the path of a strap through the chafe.

FIG. 10A shows a user engaging the connectors of two ends of a strap, preparing to connect them.

FIG. 10B shows a user engaging the handles of the chafes, and elevating them, preparing to draw the chafes apart.

FIG. 10C shows the chafes now pulled apart, the strap now tightened.

FIG. 11A shows application of an embodiment of an adjustable closure device to a full sized backpack.

FIG. 11B shows application of an embodiment of an adjustable closure device to a day backpack.

FIG. 11C shows application of an embodiment of an adjustable closure device to a protective vest.

FIG. 11D shows application of an embodiment of an adjustable closure device to motorcycle full body suit.

FIG. 11E shows application of an embodiment of an adjustable closure device to protective knee pads.

FIG. 11F shows application of an embodiment of an adjustable closure device to a pair of protective pants.

FIG. 11G shows application of an embodiment of an adjustable closure device to an ankle brace.

FIG. 11H shows application of an embodiment of an adjustable closure device to a prosthetic socket.

FIG. 11I shows application of an embodiment of an adjustable closure device to a back brace.

FIG. 11J shows application of an embodiment of an adjustable closure device to a knee brace.

FIG. 11K shows application of an embodiment of an adjustable closure device to a post-operative leg brace.

FIG. 11L shows application of an embodiment of an adjustable closure device as a built-in belt for a pair of pants.

FIG. 11M shows application of an embodiment of an adjustable closure device as a belt for a pair of pants.

DETAILED DESCRIPTION

Overview and Terminology

Figure 1A:
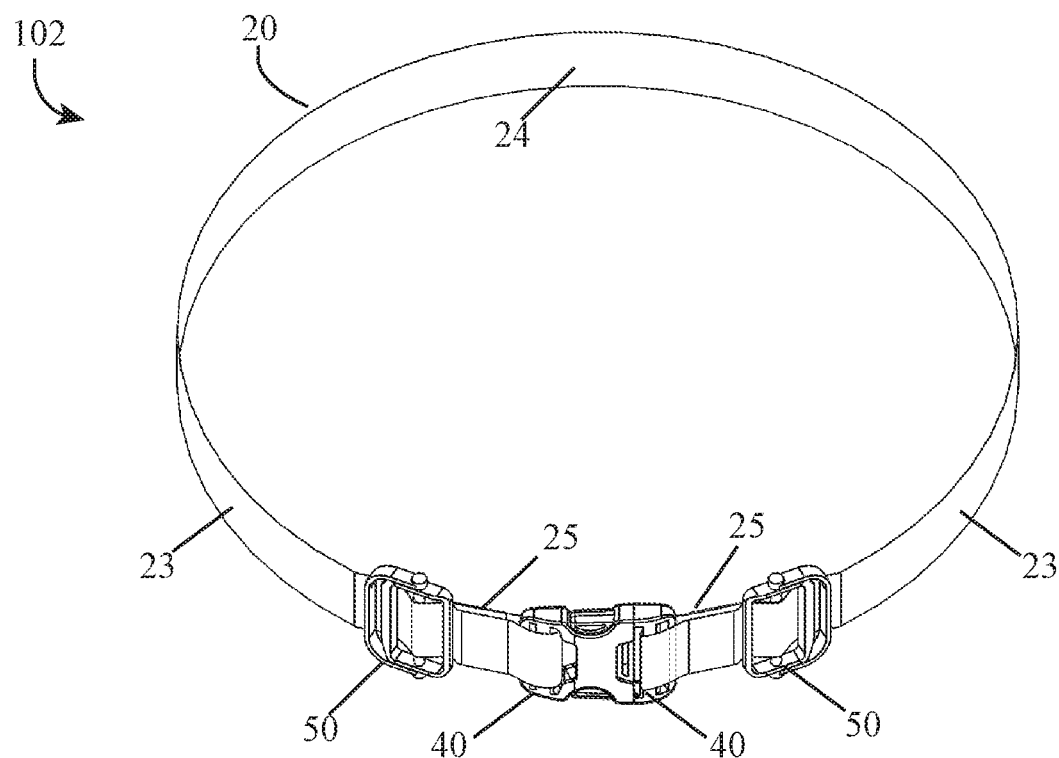
FIGS. 1A-1B show top perspective views of an embodiment of an adjustable closure device in two convertible configurations, a large circumference configuration and a small circumference configuration.
Figure 1B:
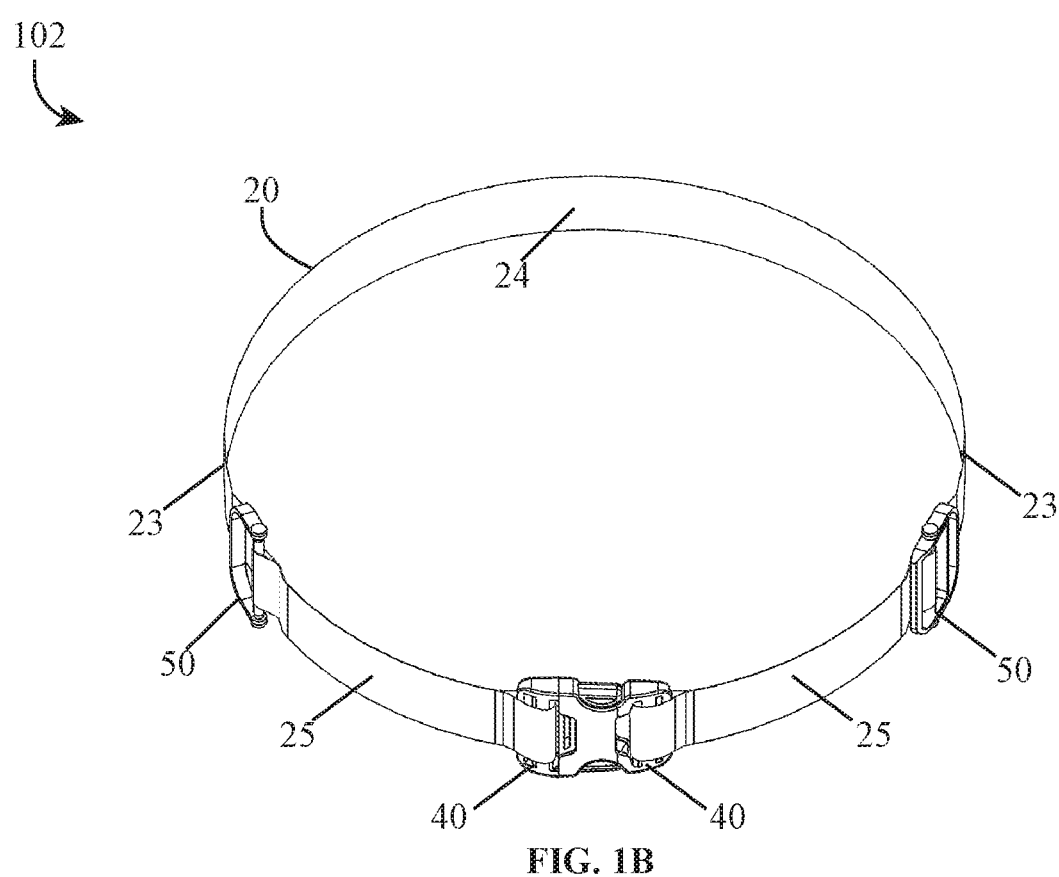

Embodiments of an adjustable closure device are depicted in FIGS. 1A-11M. FIGS. 1A-1B are particularly helpful in setting out aspects of terminology used herein, which distinguishes aspects of various embodiments provided. Embodiments of adjustable closure devices are commonly depicted with straps in a connected state, connected by mutually connectable connectors, as in the embodiment of FIGS. 1A-1B. As shown, the adjustable closure device embodiment includes a single continuous strap, with the connectors positioned at each end of the strap, and a chafe with a handle positioned on the strap near a connector. Accordingly, each strap has two end regions, and a central region between the two end regions. The end region includes a terminus, typically attached to a central bar in a chafe. The strap's end regions may both be adjustable in length by virtue of the strap interaction of each connectors with its nearby chafe, and the arrangement of the path strap through the connector and chafe. The length of the strap between the connector and the chafe may be considered an adjustable region of the strap, in which the strap is present in the form of two overlapping sections.

In some embodiments of the adjustable closure device, only one of the two end regions is adjustable by way of the connector-chafe interaction. The non-adjustable end region, although it has a connector that's compatible with the connector on the adjustable end region, may simply have no length-adjustable features. In another embodiment, an adjustable end region may not connect with a strap, per se, but rather directly to an article.

Some embodiments of the adjustable closure device do not necessarily have a single continuous strap. The central region of a strap may be intervened by another article, which, of course, needs to be able to efficiently translate tension applied to it by the end regions of the strap, thereby creating a continuous strap functionality.

Adjustability of a strap's adjustable region, when connectors are connected, translates into adjustability of a circumference enclosed by the strap. Accordingly, an adjustable closure device can assume a large circumference configuration and small circumference configuration, and move between the large and small circumferences, and stabilize at any circumference between large and small. Typically, a user engages an adjustable closure device when it is in the large circumference configuration, and manually adjusts to a small circumference configuration.

As described in a method provided herein, a user moves the adjustable closure device between the large and small configurations by manually operating a handle on the chafe, and thereby sliding the chafe with respect to the strap on which it is mounted. Chafe handles, in cooperation with the chafe as a whole, as provided herein, may be structurally configured to serve two basic functions: (1) to move the chafe with respect to the strap, and (2) to engage or disengage a friction locking mechanism that resists slippage of the chafe on the strap. Slippage is a default tendency when the strap is under tension, as may occur in a small circumference configuration. Handle embodiments are typically connected to the chafe, and include a hinge which allows the handle to assume a down position or an elevated position. Typically, the down position is a locking position that prevents strap slippage, and the elevated position is an unlocked position that allows strap slippage.

The chafe handles of adjustable closure devices, as provided herein, typically have an ergonomic structure and consequent ergonomic functionality. "Ergonomic" refers to ease and comfort as held in the hands of a user, and ease in comfort in manipulating an adjustable closure device. Adjustable closure devices can be small and difficult to manipulate by people, who may, for example, have hands that are relatively large and have difficulty manipulating small objects, or by people with hands that are relatively small, and/or people whose hands have insufficient strength to allow easy grasping and manipulation of an object.

As enumerated below in the "Embodiment List" section, and as depicted in FIGS. 1A-11M, four basic structural embodiments of an adjustable closure device 100 are provided. These structural embodiments, as defined by key features, include (1) an adjustable closure device 101 with unilateral adjustability, (2) an adjustable closure device 102 with bilateral adjustability, (3) an adjustable closure device 101P with unilateral adjustability and a chafe that provides mechanical advantage to a strap being pulled by a user to reduce the circumference enclosed by the strap or distance spanned by the strap, and (4) an adjustable closure device 102P with bilateral adjustability and a chafe that provides a mechanical advantage to a strap being pulled by a user to reduce the circumference enclosed by the strap, Each of these basic structural embodiments may further include a strap friction-locking mechanism, of which there are several types: (1) an integrated chafe handle and central bar of the chafe, the central bar configured as a one-sided cam, (2) an integrated handle and central bar of the chafe, the central bar configured as a two-sided cam, (3) a chafe with a two-part handle, a spring controlling the separation of the two handle parts, (4) a handle with a base configured as a cam, the handle and the central bar being separate pieces.

Additionally, a method of manually adjusting the circumference of the device is provided.

Figures that Exemplify Adjustable Closure Device Embodiments

FIGS. 1A-1B show top perspective views of an embodiment of an adjustable closure device 102 in two convertible configurations; FIG. 1A shows a large circumference configuration and FIG. 1B shows a small circumference configuration. Adjustable closure device 102 includes a strap 20, with strap end regions 22 and a central region 24, and adjustable regions 25. Adjustable closure device 102 further includes two connectors 40 (connected together) and two chafes 50.

Strap adjustable regions 25 are bounded by their respective connector 40 and chafe 50. In FIG. 1A, where adjustable closure device 102 is in a large circumference configuration, the two adjustable regions are short. In FIG. 1AB, where adjustable closure device 102 is in a small circumference configuration, the two adjustable regions are long.

Figure 2A:
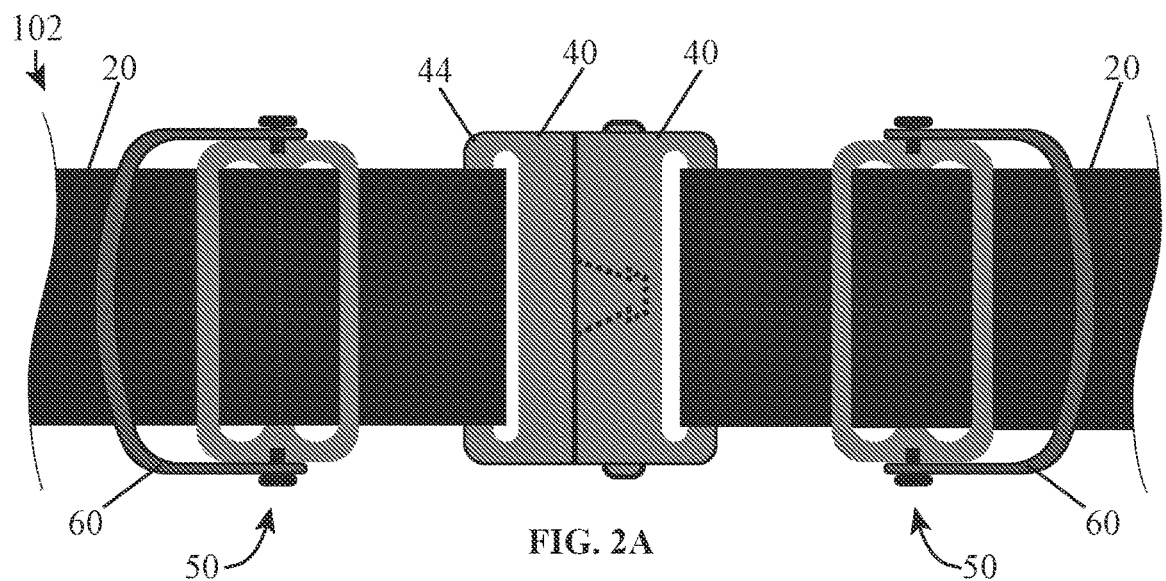
FIGS. 2A-2C are views of an embodiment of an adjustable closure device.
Figure 2B:
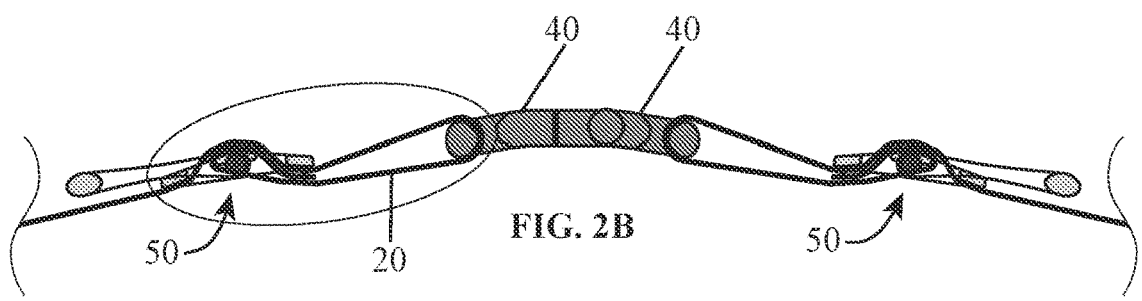
Figure 2C:
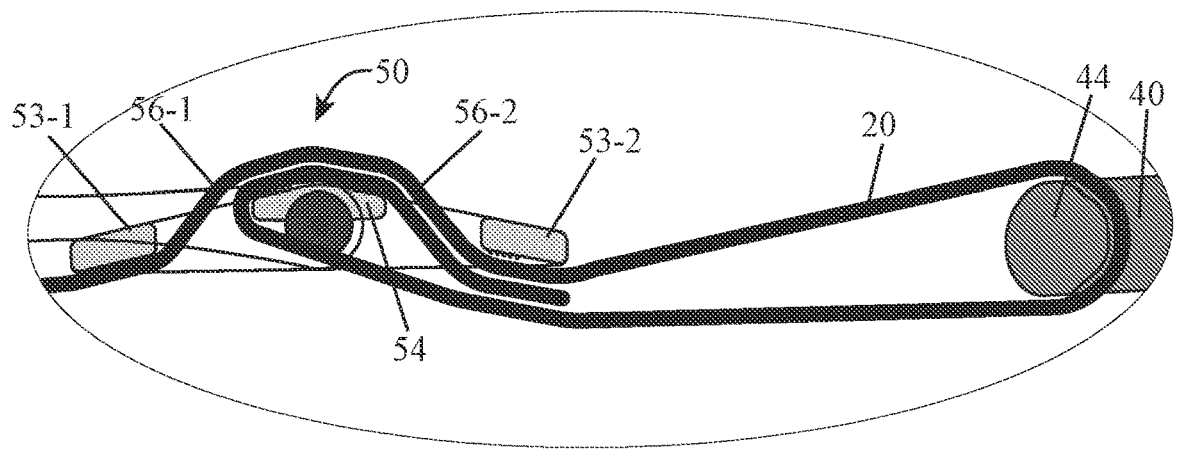

FIGS. 2A-2C are views of an embodiment of a bilateral adjustable closure device 102. FIG. 2A is a face view that shows the two end regions of a strap 20, the straps connected by mutually connectable connectors 40 (each connector having a strap pivot bar 44) and a chafe 50 disposed on both straps into which the strap ends terminate. Chafe 50 has a handle 60. "Bilateral" refers to a device configuration in which both ends of a strap (or the strap on both sides of engaged connectors) are adjustable. Inasmuch as FIG. 2C shows only a single chafe and connector, FIG. 2C can also represent an aspect of a unilateral adjustable closure device 101.

FIG. 2B is a side view of adjustable closure device 102; FIG. 2C is a detailed view of the left-hand portion of FIG. 2B, focusing on the path of strap 20 through chafe 50 and connector 40, as well as showing chafe 50 in some detail. Chafe 50 includes a first outer bar 53-1, a central bar 54, and a second outer bar 53-2. First outer bar 53-1 and central bar 54 define a strap pass through gap 56-1; second outer bar 53-2 and central bar 54 define a strap pass through gap 56-2.

The path of strap 20 through chafe 50 and connector 40 as shown in FIG. 2B, and in greater detail in FIG. 2C is as follows. Each strap end-region provides a strap path in which strap segments arranged, directionally from the strap's central region toward a strap terminus 23 at the central bar 54 of chafe 50, to (a) pass through the first chafe gap 56-1, (b) pass by central chafe bar 54, (c) pass through the second chafe gap 56-2, (d) loop around pivot bar 44 of connector 40, and then (e) return toward chafe 50, to loop around and attach to central bar 54 of chafe 50.

Figure 3A:
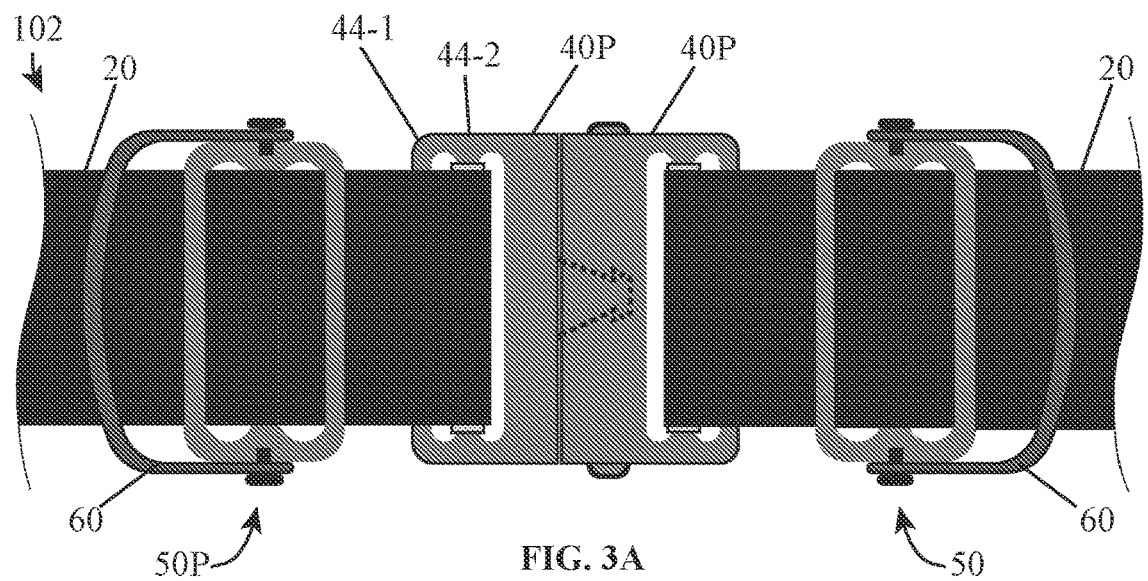
FIGS. 3A-3C show views of an embodiment of an adjustable closure device with bilateral strap adjustability, showing in particular, the path of a strap through the connectors and chafes within the device.
Figure 3B:
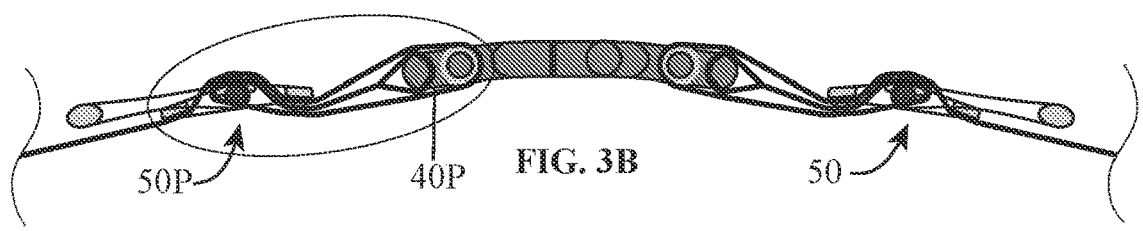
Figure 3C:
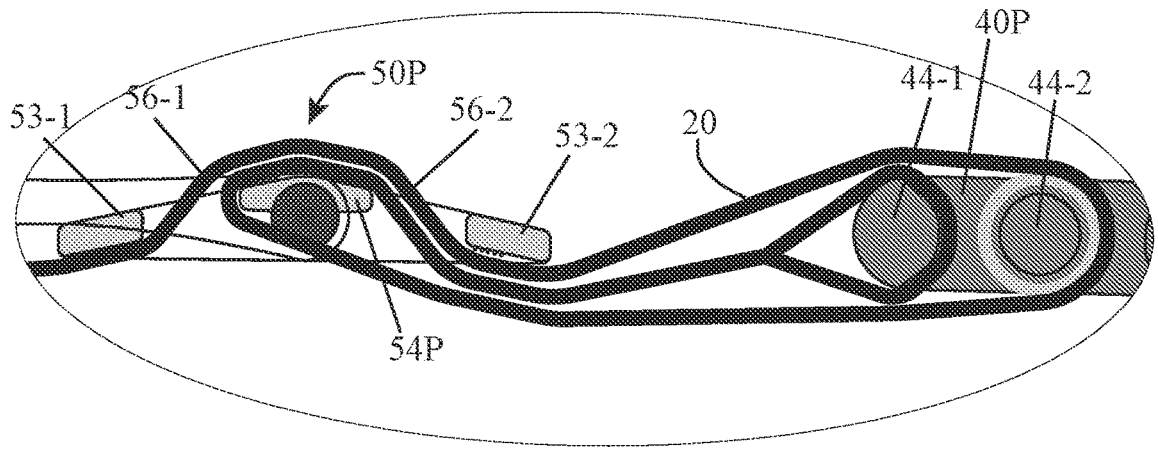

FIGS. 3A-3C show views of an embodiment of an adjustable closure device 102P with bilateral strap adjustability and with the strap configured as a pulley, showing in particular, the path of a strap through the connectors and chafes within the device. FIG. 3A is a face view; FIG. 3B is a side view, and FIG. 3C is a detailed view of a portion of FIG. 3B. FIG. 3A shows the two end regions of a strap 20, the straps connected by mutually connectable connectors 40P (each connector having a first strap pivot bar 44-1 and a second pivot bar 44-2), and a chafe 50P disposed on both straps into which the strap ends terminate, chafe 50P having a handle 60. Inasmuch as FIG. 3C shows only a single chafe and connector, FIG. 3C can also represent an aspect of a unilateral adjustable closure device 101P.

Adjustable closure device 102P differs from adjustable closure device 102 (FIGS. 2A-2C) because strap 20 of 102P is configured as a pulley with a 2:1 mechanical advantage in terms of the manual force a user needs to apply to chafe handle 60 to move the strap from a large circumference toward a smaller circumference. Details of the strap pulley arrangement are shown in the side views of FIG. 3B-3C.

FIG. 3B shows a pulley arrangement that involves chafe 50P, connector 40P, and the path of strap 20 through both chafe 50P and connector 40P. The path of strap 20 through chafe 50P and connector 40P as shown in FIG. 3B, and in greater detail in FIG. 3C is as follows. Each strap end-region provides a strap path in which strap segments arranged, directionally from the strap's central region toward a strap terminus at connector 40P, to (a) pass through the first chafe gap 56-1, (b) pass by the central chafe bar 56-1, (c) pass through the second chafe gap 56-2, (d) pass toward connector 40P, to loop around the connector's second pivot bar 44-2, (e) returning toward chafe 50P, to pass around central bar 54P of the chafe, and (f) returning toward connector 40P to loop around and terminate the connector's second pivot bar 44-2. This strap and pivot arrangement, wherein the strap reverses direction twice, is a pulley arrangement that provides a 2-fold mechanical advantage in terms of force required to move the strap from a large circumference toward a smaller circumference.

Figure 4A:
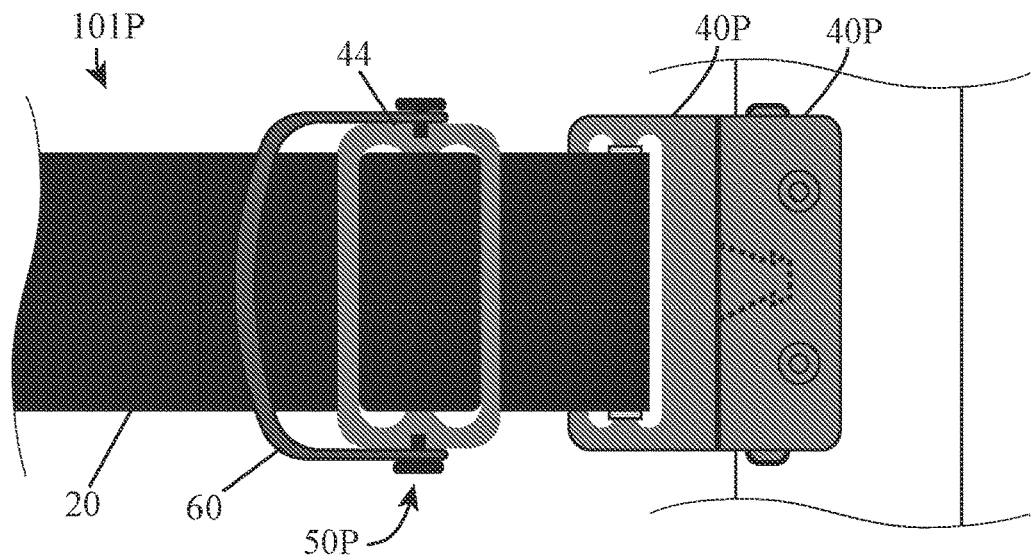
FIGS. 4A-4C show views of an embodiment of an adjustable closure device with unilateral strap adjustability and double loop of strap between a connector and a chafe, thereby conferring a mechanical advantage, showing in particular, the path of a strap through the connectors and chafes within the device.
Figure 4B:
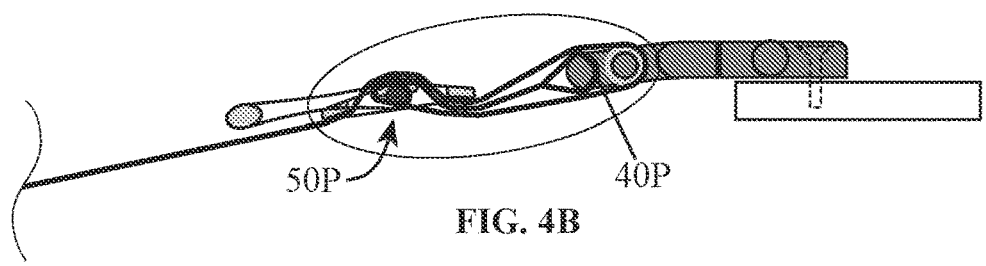
Figure 4C:
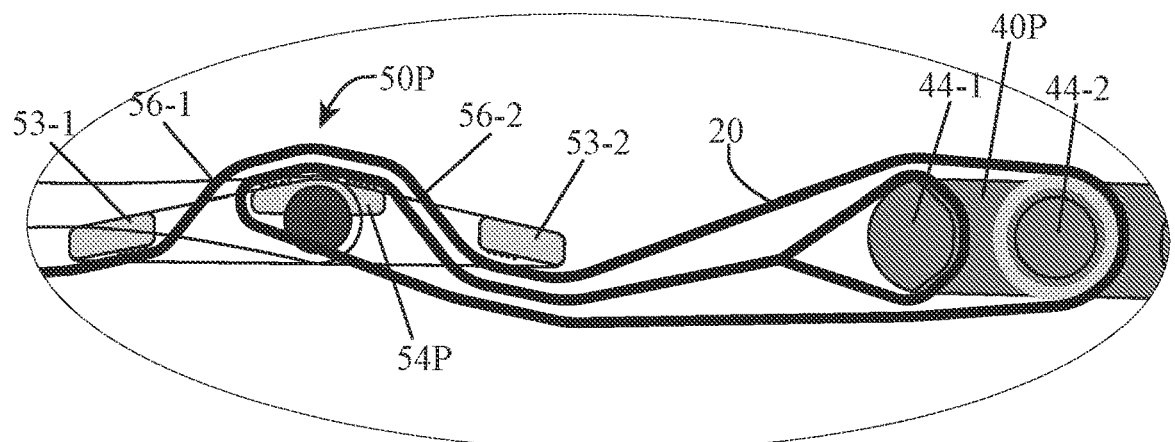

FIGS. 4A-4C show views of an embodiment of an adjustable closure device 101P with unilateral strap adjustability and with the strap configured as a 2:1 pulley system, showing in particular, the path of a strap through the connectors and chafes within the device. "Unilateral" refers to a device configuration in which end of a strap (or the strap on only one side of engaged connectors) is adjustable. FIG. 4A is a face view; FIG. 4B is a side view, and FIG. 4C is a detailed view of a portion of FIG. 4B. FIG. 4A shows the two end regions of a strap 20, the straps connected by mutually connectable connectors 40P (the connector having a first strap pivot bar 44-1 and a second pivot bar 44-2), and a chafe 50P disposed on both straps into which the strap ends terminate, chafe 50P having a handle 60.

Adjustable closure device 102P differs from adjustable closure device 102 (FIGS. 2A-2C) because the strap is configured as a pulley, thereby providing a 2:1 mechanical advantage in terms of the manual force a user needs to apply to chafe handle 60 to move the strap from a large circumference toward a smaller circumference or from a longer strap to a shorter strap, if the strap adjustment is linear or not circumferential. Details of the strap pulley arrangement are shown in the side views of FIG. 3B-3C.

FIG. 4B shows a pulley arrangement that involves chafe 50P, connector 40P, and the path of strap 20 through both chafe 50P and connector 40P. The path of strap 20 through chafe 50P and connector 40P as shown in FIG. 3B, and in greater detail in FIG. 4C is as follows. Each strap end-region provides a strap path in which strap segments arranged, directionally from the strap's central region toward a strap terminus at the central bar 54 of chafe 40, to (a) pass through the first chafe gap 56-1, (b) past the central chafe bar 54, (c) through the second chafe gap 56-2, (d) around a second pivot bar 44-1 of connector 40P, (e) returning toward chafe 50P and thence around the central bar 54 of chafe 50P, and (f) in a return direction, toward the strap's central region, to loop around and attach to the first pivot bar 44 of connector 40P. This strap and pivot arrangement, wherein the strap reverses direction twice, is a pulley arrangement that provides a 2-fold mechanical advantage in terms of force required to move the strap from a large circumference toward a smaller circumference or from a longer strap to a shorter strap, if the strap adjustment is linear or not circumferential.

Figure 5A:
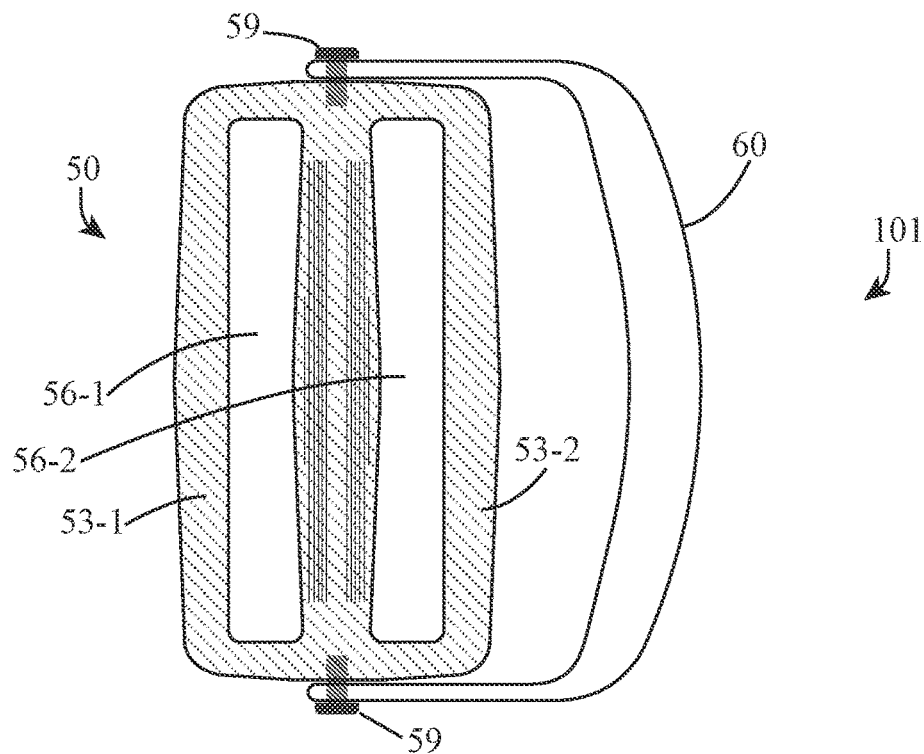
FIGS. 5A-5E show views of an embodiment of an adjustable closure device, showing in particular, views of the path of a strap through a connector and a chafe within the device.
Figure 5B:
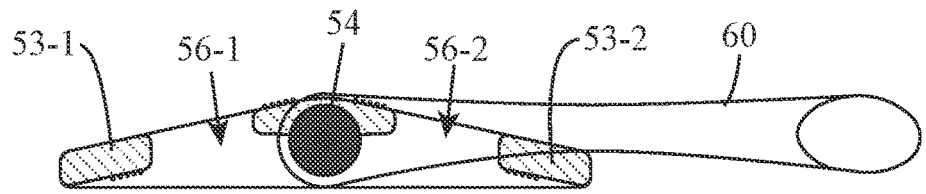
Figure 5C:
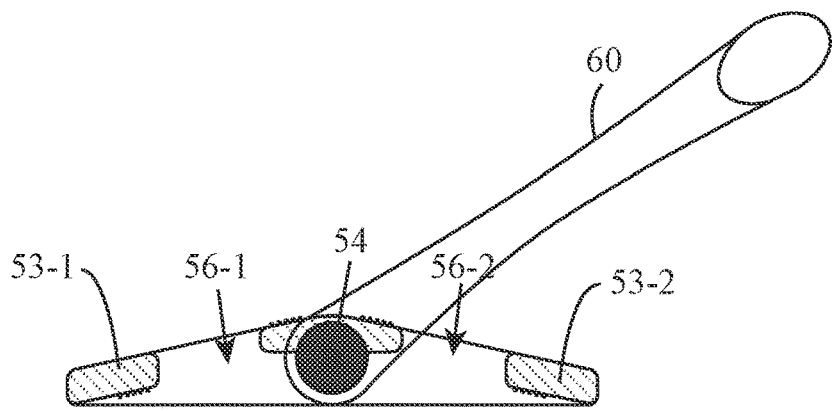
Figure 5D:
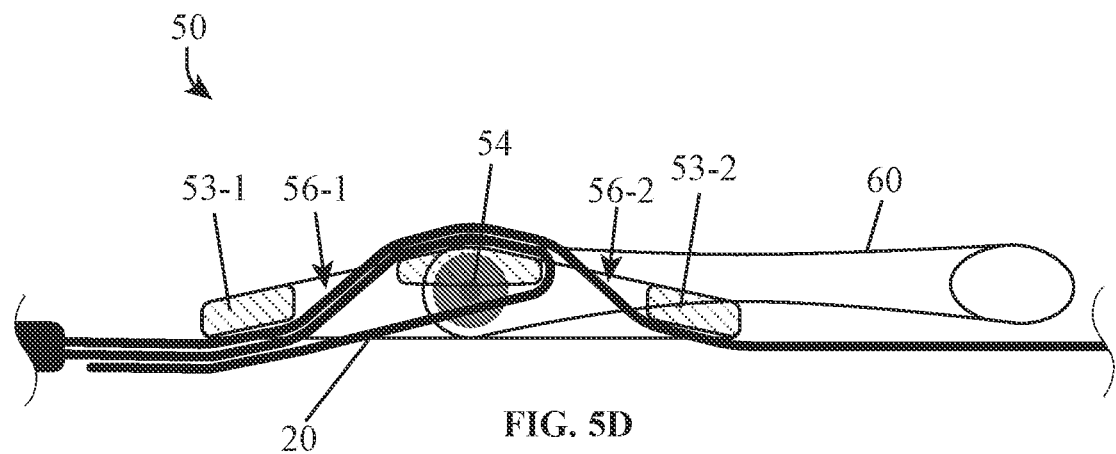
Figure 5E:
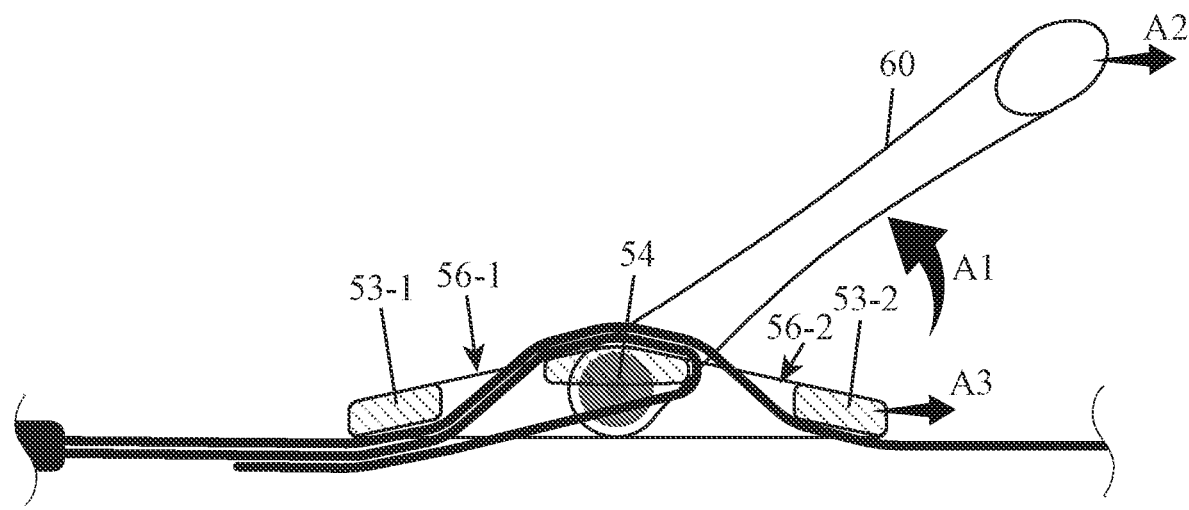

FIGS. 5A-5E show views of an embodiment of an adjustable closure device 101, showing in particular, views of the path of a strap through a connector and a chafe within the device. FIG. 5A is a face view of a chafe 50 and hinged handle 60. FIG. 5B is a side view of a chafe and hinged handle, with handle 60 in a down position, and FIG. 5C is a side view of a chafe and hinged handle, with handle 60 in an elevated position. FIGS. 5D-5E both show a side view of a chafe and hinged handle and the path of a strap through chafe 50. In FIG. 5D, the handle is in a down position; in FIG. 5E, the handle is in an elevated position. Inasmuch as FIGS. 5A-5E show only a single chafe 50, these figures can represent also an aspect of a bilateral adjustable closure device 102.

Chafe 50 includes two outer bars, a first outer bar 53-1 (on the left as shown), a second outer bar 53-2 (on the right as shown), and a central bar 54. The left side of chafe 50 is also the side on which a connector (not shown) is positioned. The right side of chafe 50 is the central side of the chafe, the side which is proximate the central region of the strap (FIGS. 1A-1B).

Chafe 50 further includes a handle 60. Handle 60 includes a handle base which, in this embodiment, is integral with central bar 54. A hinge 59 connects handle 60 to central bar 54 (also the base handle 60) and, accordingly, to chafe 50, which allows the handle to rotate between a down position (as in FIGS. 5B and 5D) and an elevated position (as in FIGS. 5C and 5E).

FIGS. 5D and 5E are similar to 5B and 5D, respectively, except that FIGS. 5D and 5E show the path of strap 20 through chafe 50. Arrow A1 shows directionality of handle 60 elevating; arrow A2 shows the direction of a manual pull that is allowed when handle 60 is in the elevated position; arrow A3 shows the direction that chafe 50 moves along strap 20, when the handle is elevated (A1) and being pulled (A2). A manual pull, per arrow A2, pulls chafe 50 along strap 20, away from the connector and closer to the central region of strap 20. According, by a user manipulating handle 60 (per arrows A1, A2, and A3), the user can move adjustable closure device 101 between a large circumference configuration and a small circumference configuration.

FIGS. 6A-6E show views of an embodiment of an adjustable closure device 101-C1 with a handle 60-C1 that is integrated with the central bar 54-C1 of a chafe 50-C1, the central bar being a one-sided cam that acts as a component of a friction-based strap lock. The "C1" designation refers to an embodiment that has a handle with a base, the base being integral with a chafe central bar that is configured as a 1-sided cam, as described below.

Figure 6A:
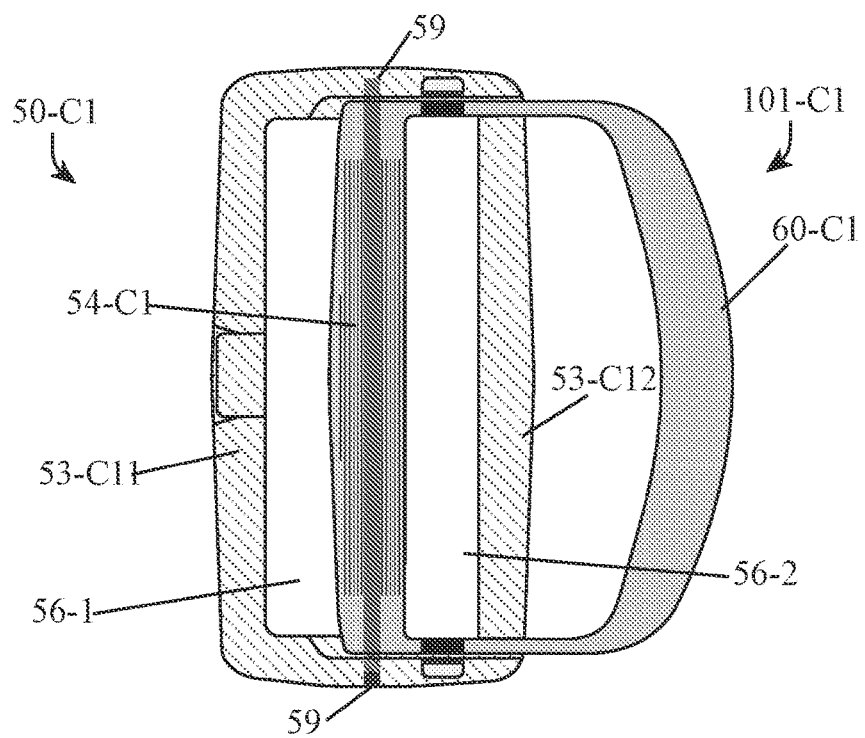
FIGS. 6A-6E show views of an embodiment of an adjustable closure device with a handle having an integrated one-sided cam that acts as friction-based strap lock.
Figure 6B:
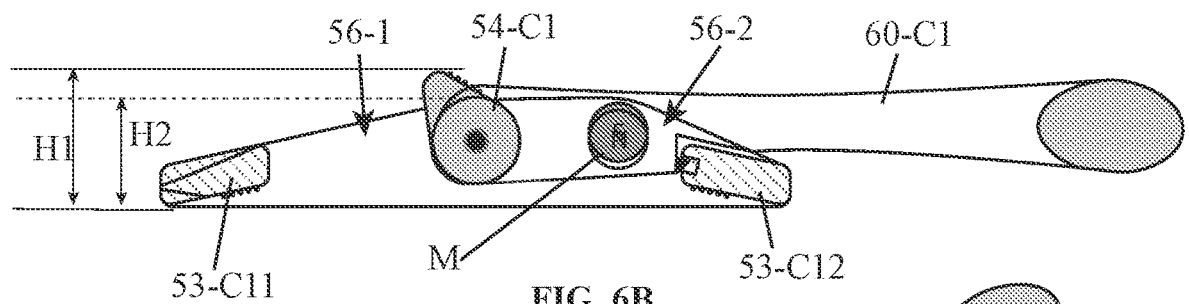
Figure 6C:
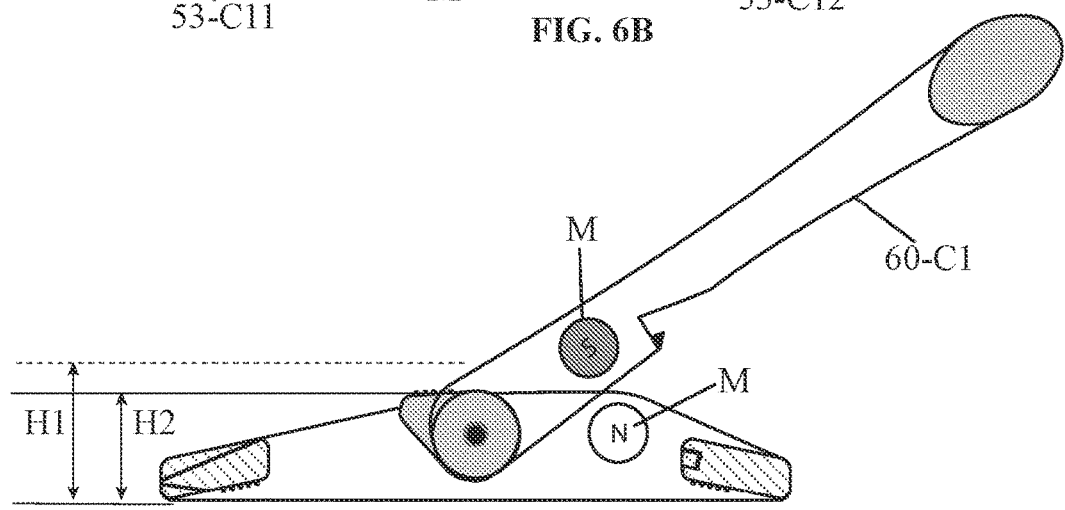
Figure 6D:
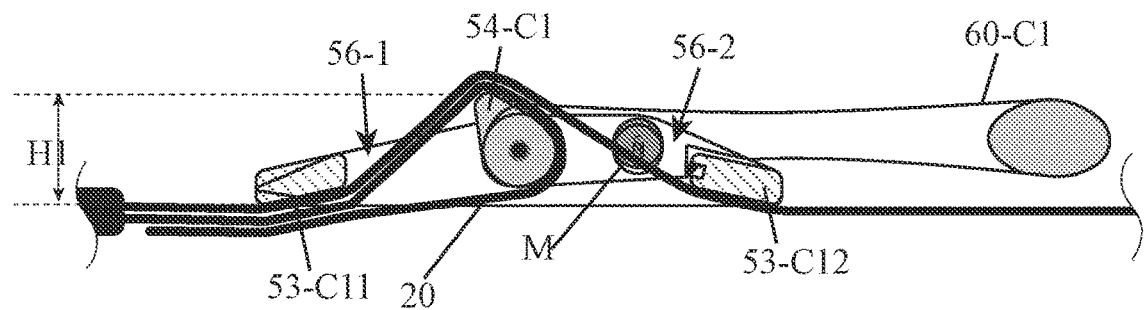
Figure 6E:
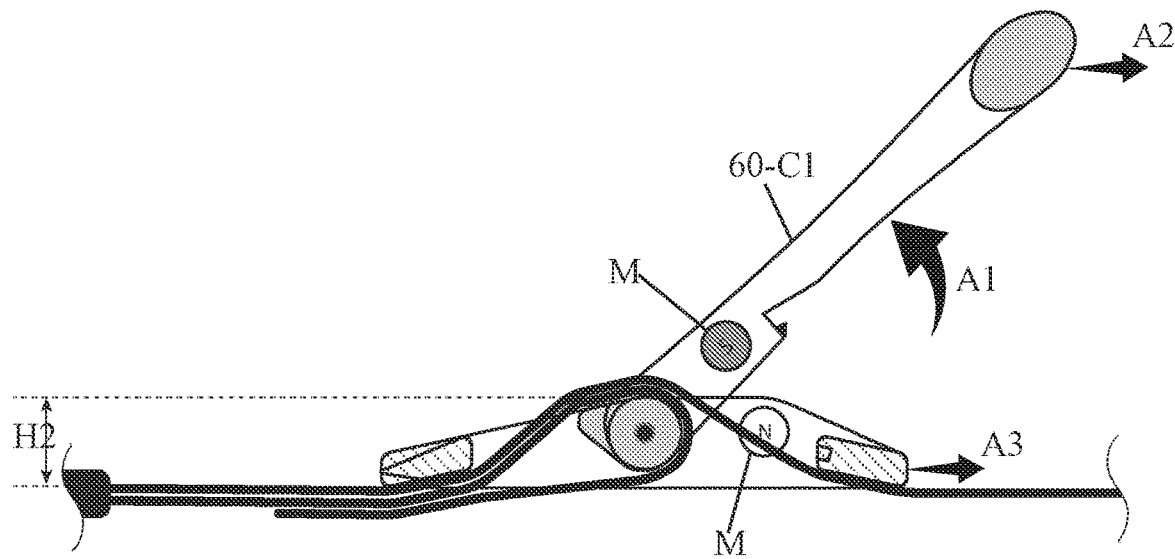

FIG. 6A is a face view of a chafe 50-C1 applicable to this embodiment. FIG. 6B is a side view showing the handle in a down position; FIG. 6C is a side view showing a handle 60-C1 in an elevated position. FIG. 6D is a side view showing handle 60-C1 in a down position, and further showing the path of a strap 20 through the chafe. FIG. 6E is a side view of showing handle 60-C1 in an elevated position, and further showing the path of a strap 20 through the chafe. FIGS. 6D-6E both show a side view of a chafe 50-C1 and hinged handle 60-C1 and the path of a strap through chafe 50-C1. In FIG. 6D, handle 60-C1 is in a down position; in FIG. 6E, the handle is in an elevated position. Inasmuch as FIGS. 6A-6E show only a single chafe 50-C1, these figures can represent also an aspect of a bilateral adjustable closure device 102-C1.

Chafe 50-C1 is applicable to both unilaterally adjustable embodiments, such as this one, and to bilaterally-adjustable adjustable closure devices as also described herein.

Chafe 50-C1 includes two outer bars, a first outer bar 53-C11 (on the left as shown), a second outer bar 53-C12 (on the right as shown), and a central bar 54-C1, which includes a high friction surface of the cam, as indicated by the striated lines. The left side of chafe 50-C1 is also the side on which a connector (not shown) is positioned. The right side of chafe 50-C1 is the central side of the chafe, the side which is proximate the central region of the strap (see FIGS. 1A-1B).

Chafe 50-C1 further includes a handle 60-C1. Handle 60-C1 includes a handle base which, in this embodiment, is integral with (one and the same as) central bar 54-C1, and which is configured a 1-sided cam. A hinge 59 connects handle 60-C1 to central bar 54-C1 (also the base of handle 60-C1) and, accordingly, to chafe 50-C1, which allows the handle to rotate between a down position (as in FIGS. 6B and 6D) and an elevated position (as in FIGS. 6C and 6E). When handle 60-C1 is in a down position, its position is stabilized or retained by a retention mechanism, exemplified by a pair of magnets M (labeled separately as N and S) that are disposed on apposing sides of handle 60-C1 and chafe 50-C1.

FIGS. 6D-6E are similar to FIGS. 6B-6D, respectively, except that FIGS. 6D and 6E further show the path of strap 20 through chafe 50-C1. Arrow A1 shows the directionality of handle 60-C1 elevating; arrow A2 shows the direction of a manual pull that is allowed when handle 60-C1 is in the elevated position; arrow A3 shows the direction that chafe 50 moves along strap 20, when the handle is elevated (A1) and being pulled (A2). A manual pull, per arrow A2, pulls chafe 50-C1 along strap 20, away from the connector and closer to the central region of strap 20. According, by a user manipulating handle 60-C1 (per arrows A1, A2, and A3), the user can move adjustable closure device 101-C1 between a large circumference configuration and a small circumference configuration.

Rotation of handle 60-C1 results in the rotation of central bar 54-C1 (one and the same as the base of handle 60-C1, which changes the peak height of its one-sided cam portion (FIGS. 6B-6D). When handle 60-C1 is in a down position (FIG. 6B) the peak height corresponds to arrow H1; when handle 60-C1 is in an elevated position (FIG. 6C), the peak height corresponds to arrow H2, which is lower than H1. "Height", in this context, refers to the distance between the peak of the one-sided cam over a baseline defined by the bottom of outside bars of chafe 50-C1. These differences in height are reflected in the path of strap 20 (FIGS. 6D-6E). The greater height H1 causes a change in the pathway of strap 20 through the chafe 50-C1. When handle 60-C1 is in the down position, the increased height H1 causes a corresponding steeper angle in the path of strap 20 and consequent higher frictional force between strap 20 and chafe 50-C1 as the strap passes through gaps 56-1 and 56-2 between center bar 54-C1 and two outside bars 53-C11 and 53-C12. This height-elevating feature increases the tension retaining capacity of chafe 50-C1 when the handle is in the down configuration as compared to a reduced frictional configuration when the handle is elevated. The lower height H2, when the handle is elevated, in contrast, allows easy movement of the strap through the chafe, allowing a change in the size of the adjustable region of the strap, and consequent change in the circumference enclosed by the strap. Accordingly, this cooperative aspect of the handle and the central bar of the chafe and the consequent effect on the strap path through the chafe constitutes and embodiment of a friction-lock.

FIGS. 7A-7F show views of an embodiment of an adjustable closure device 101-C2 with a handle 60-C2 integrated with the central bar 54-C2 of a chafe 50-C2, the central bar being a two-sided cam that acts as a component of friction-based strap lock. The "C2" designation refers to an embodiment that has a handle with a base, the base being integral with a chafe central bar that is configured as a 2-sided cam, as described below.

Figure 7A:
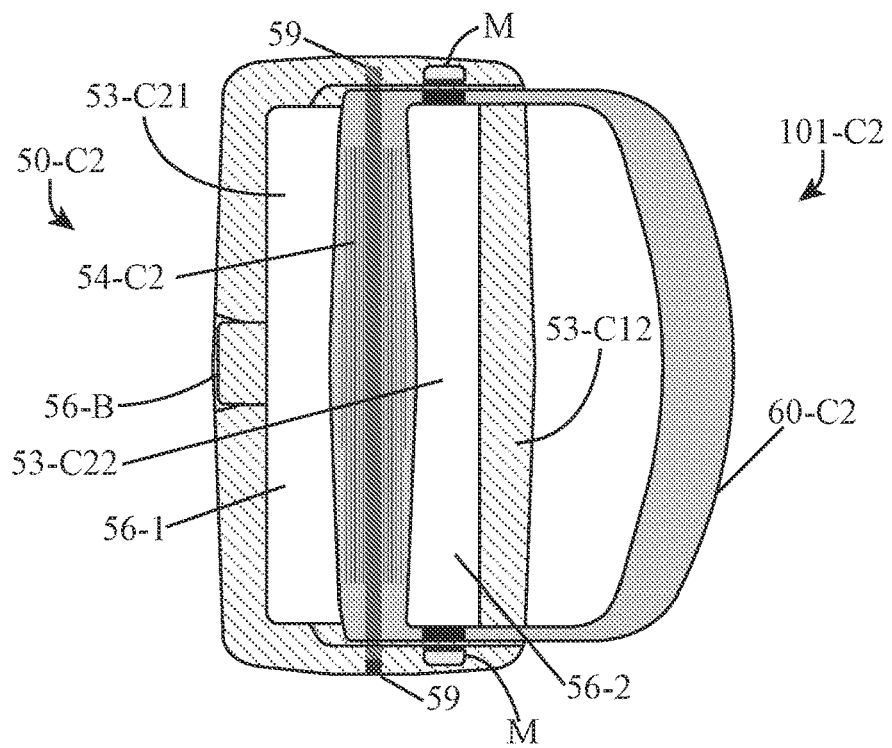
FIGS. 7A-7F show views of an embodiment of an adjustable closure device with a chafe having a central bar configured as a two sided cam that acts as friction-based strap lock.
Figure 7B:
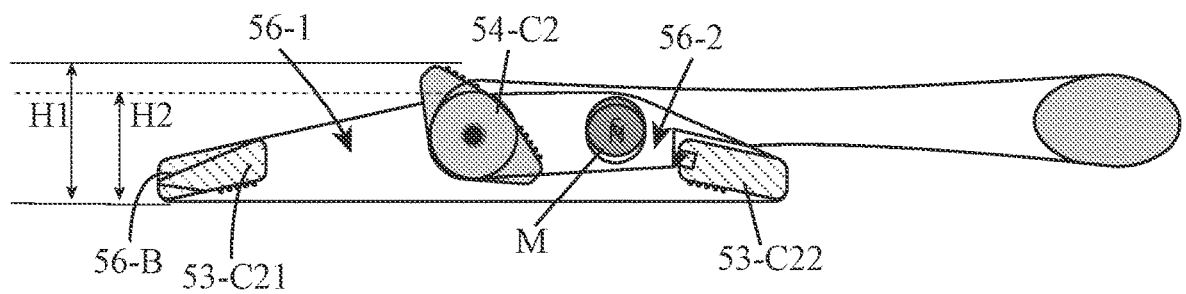
Figure 7C:
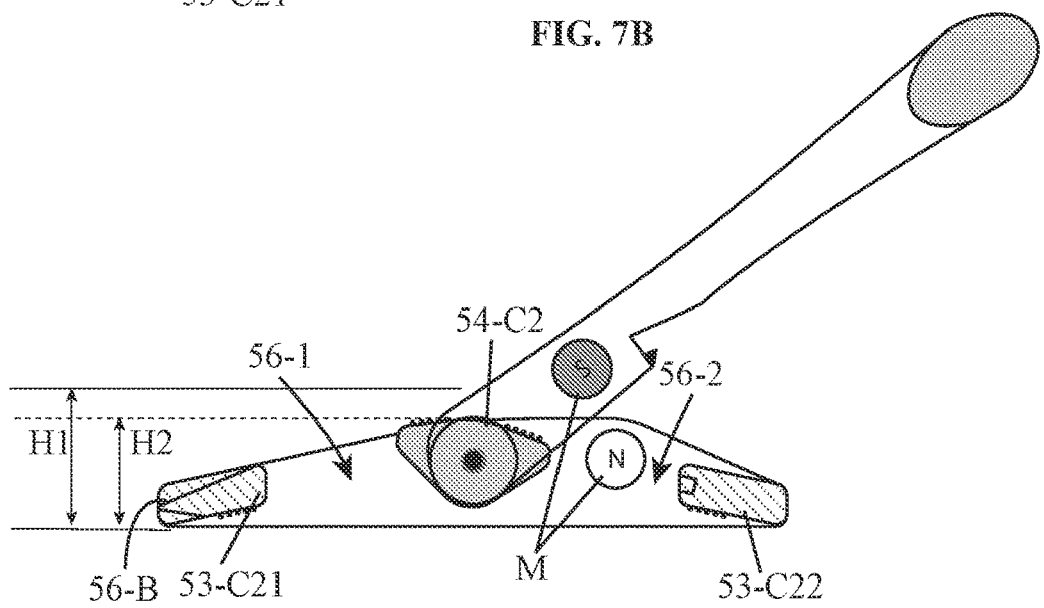
Figure 7D:
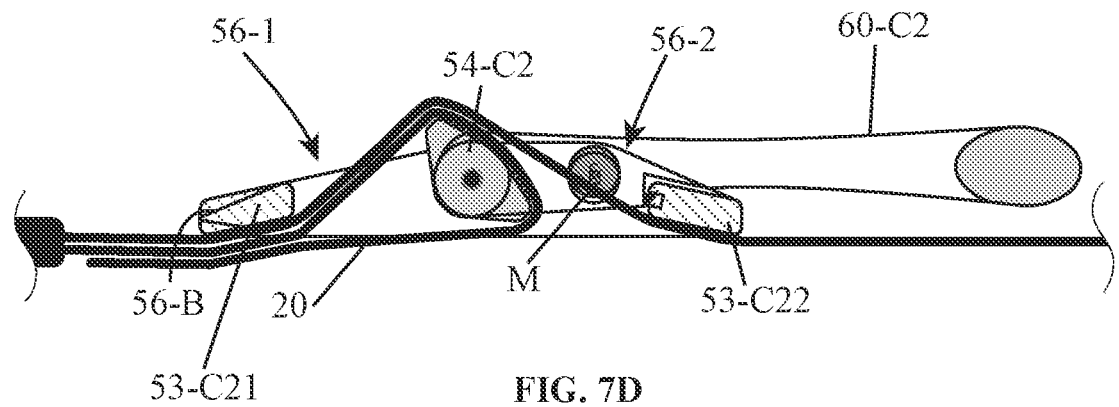
Figure 7E:
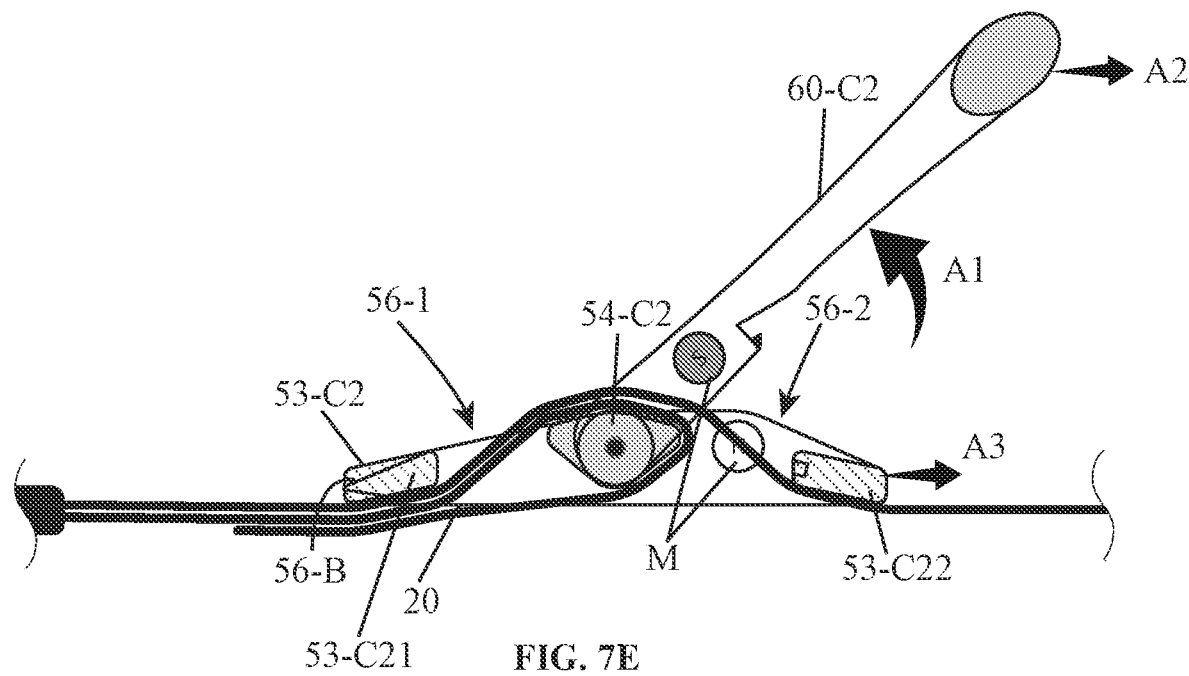

FIG. 7A is a face view of a chafe 50-C2 applicable to this embodiment. FIG. 7B is a side view showing the handle in a down position; FIG. 7C is a side view showing a handle 60-C2 in an elevated position. FIG. 7D is a side view showing handle 60-C1 in a down position, and further showing the path of a strap 20 through the chafe. FIG. 7E is a side view of showing handle 60-C2 in an elevated position, and further showing the path of a strap 20 through the chafe. FIGS. 7D-7E both show a side view of a chafe 50-C2 and hinged handle 60-C1 and the path of a strap through chafe 50-C2. In FIG. 7D, handle 60-C2 is in a down position; in FIG. 7E, the handle is in an elevated position. Chafe 50-C2 is applicable to both unilaterally adjustable embodiments, such as this one, and to bilaterally-adjustable adjustable closure devices as also described herein.

Figure 7F:
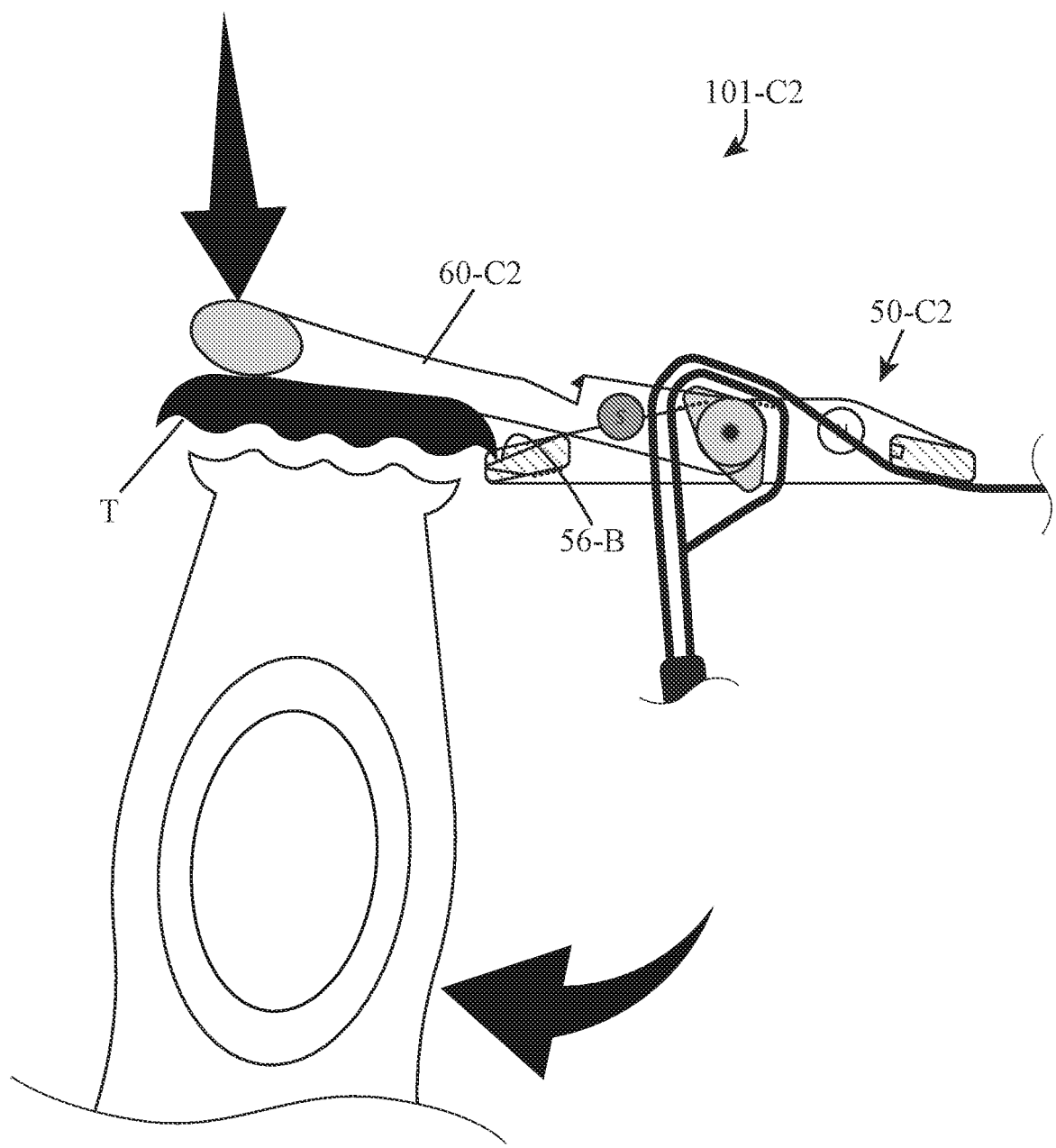

FIG. 7F is a side view of an embodiment of an adjustable closure device with a chafe having a central bar configured as a two sided cam that acts as friction-based strap lock, and with a tool T attached to the bottom side of the handle. In this embodiment, tool T is a bottle opener, hereby applied to a bottle. A surface feature 56-B is shown on outer bar 53-1 that cooperates the bottle opener T to open a bottle.

Chafe 50-C2 includes two outer bars, a first outer bar 53-C21 (on the left as shown), a second outer bar 53-C22 (on the right as shown), and a central bar 54-C2, which includes a high friction surface of the cam, as indicated by the striated lines. The left side of chafe 50-C2 is also the side on which a connector (not shown) is positioned. The right side of chafe 50-C2 is the central side of the chafe, the side which is proximate the central region of the strap (see FIGS. 1A-1B).

Chafe 50-C2 further includes a handle 60-C2. Handle 60-C2 includes a handle base which, in this embodiment, is integral with central bar 54-C4 (one and the same as), and which is configured a 2-sided cam. A hinge 59 connects handle 60-C2 to central bar 54-C2 (also the base of handle 60-C2) and, accordingly, to chafe 50-C2, which allows the handle to rotate between a down position (as in FIGS. 7B and 7D) and an elevated position (as in FIGS. 7C and 7E). When handle 60-C2 is in a down position, its position is stabilized or retained by a retention mechanism, exemplified by a pair of magnets M (labeled separately as N and S) that are disposed on apposing sides of handle 60-C2 and chafe 50-C2.

FIGS. 7D-7E are similar to FIGS. 7B-7D, respectively, except that FIGS. 7D and 7E further show the path of strap 20 through chafe 50-C2. Arrow A1 shows the directionality of handle 60-C1 elevating; arrow A2 shows the direction of a manual pull that is allowed when handle 60-C1 is in the elevated position; arrow A3 shows the direction that chafe 50 moves along strap 20, when the handle is elevated (A1) and being pulled (A2). A manual pull, per arrow A2, pulls chafe 50 along strap 20, away from the connector and closer to the central region of strap 20. According, by a user manipulating handle 60-C1 (per arrows A1, A2, and A3), the user can move adjustable closure device 101-C2 between a large circumference configuration and a small circumference configuration.

Rotation of handle 60-C2 results in the rotation of central bar 54-C2 (one and the same as the base of handle 60-C2, which changes the peak height of its one-sided cam portion (FIGS. 7B-7D). When handle 60-C2 is in a down position (FIG. 7B) the peak height corresponds to arrow H1; when handle 60-C2 is in an elevated position (FIG. 6C), the peak height corresponds to arrow H2, which is lower than H1. "Height", in this context, refers to the distance between the peak of the one-sided cam over a baseline defined by the bottom of outside bars of chafe 50-C2. These differences in height are reflected in the path of strap 20 (FIGS. 7D-7E). The greater height H1 causes a change in the pathway of strap 20 through the chafe 50-C2. When handle 60-C2 is in the down position, the increased height H1 causes a corresponding steeper angle in the path of strap 20 and consequent higher frictional force between strap 20 and chafe 50-C2 as the strap passes through gaps 56-1 and 56-2 between center bar 54-C1 and two outside bars 53-C21 and 53-C22. This height-elevating feature increases the tension retaining capacity of chafe 50-C1 when the handle is in the down configuration as compared to a reduced frictional configuration when the handle is elevated. The lower height H2, when the handle is elevated, in contrast, allows easy movement of the strap through the chafe, allowing a change in the size of the adjustable region of the strap, and consequent change in the circumference enclosed by the strap. Accordingly, this cooperative aspect of the handle and the central bar of the chafe and the consequent effect on the strap path through the chafe constitutes and embodiment of a friction-lock.

FIGS. 8A-8G show views of an embodiment of an adjustable closure device 101-S with a two-part handle 64 that has a mechanism based on a spring 65 that acts as friction-based strap lock. The "S" designation refers the spring included in this embodiment. Inasmuch as FIGS. 8A-8G show only a single chafe 50-S, these figures can represent also an aspect of a bilateral adjustable closure device 102-S.

FIG. 8A is a face view of a chafe 50-S; FIG. 8B is a detailed view of FIG. 8A, focusing on the area surrounding the spring (65-S) based mechanism. Two-part handle 64 includes an outer handle 64-0, and an inner handle 64-I nested inside outer handle 64-0, and configured such that inner handle square pin 64-H is enabled to slide in outer handle slot 64-G. Outer handle 64-0 is connected to chafe 50-S by hinges 59. Chafe 50-S includes a first outer bar 53-51, second outer bar 53-S2, and central bar 54-S.

Figure 8D:
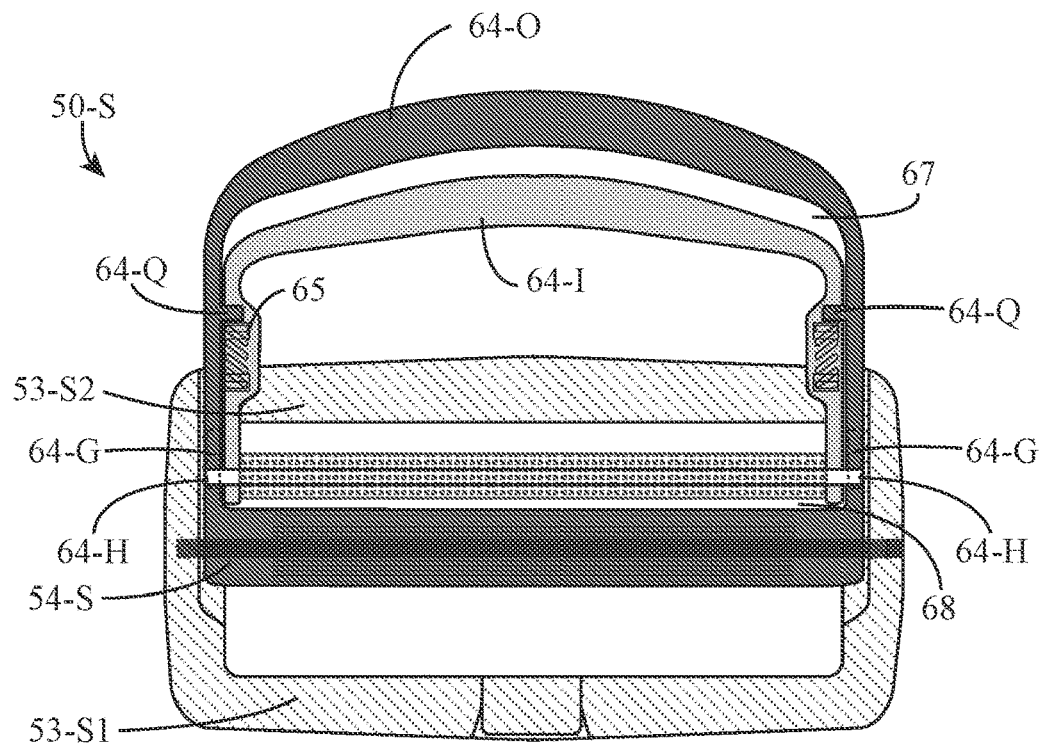
Figure 8E:
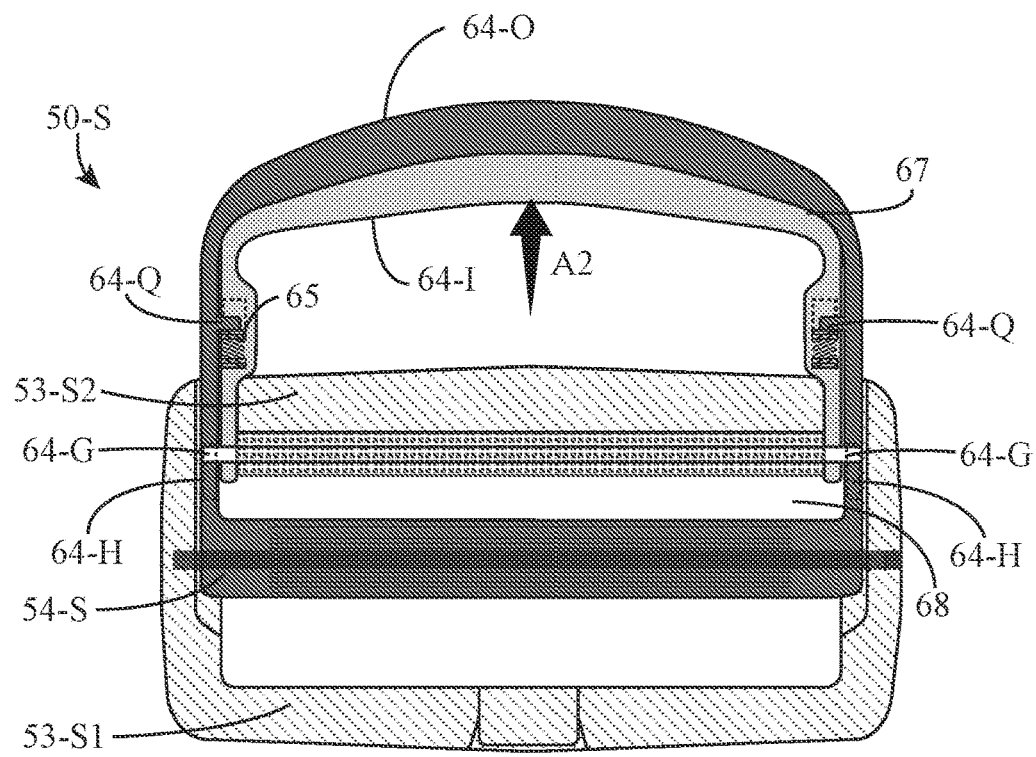

FIG. 8C is a side view showing the two-part handle 64 of the chafe in a down position. FIG. 8D is a face showing the two-parts of the handle 64 in a separated position, spring 64-S in an uncompressed configuration, and accordingly, in a locked configurations. FIG. 8E is a face view of an embodiment showing the two-parts of handle 64 in a closed position, spring 65 in a compressed configuration, and accordingly, in an unlocked configuration. Also shown is the inner-directed high-friction end 64-E of inner handle 64-I.

Figure 8F:
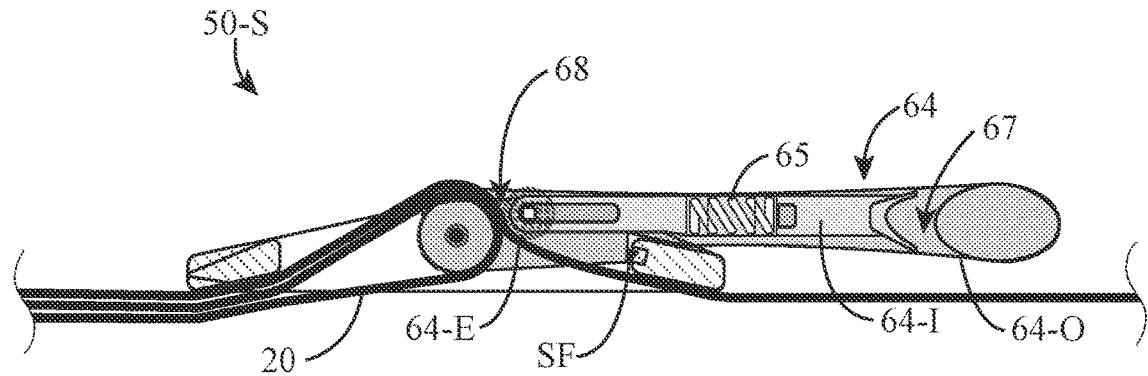
Figure 8G:
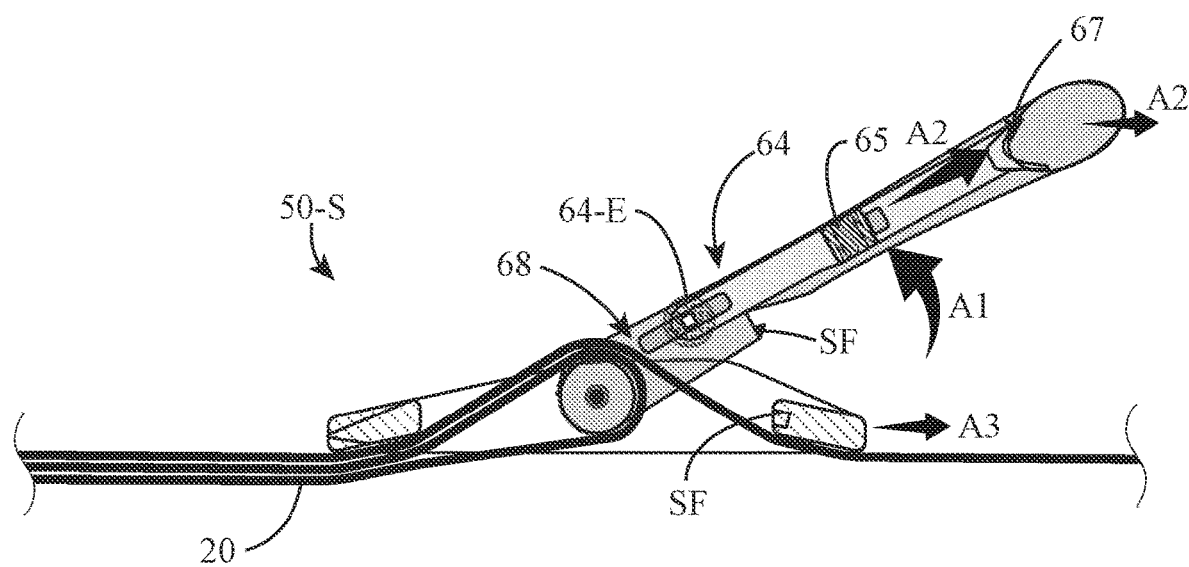

As shown in FIGS. 8F and 8G, inner handle high-friction end 64-E comprises a material having a high coefficient of friction against the material of strap 20 and is press-fit around a square pin 64-H such that it is rotationally fixed about square pin 64-H and able to slide with the inner handle. The inner handle assembly has a default configuration friction lock that is spring-based and biased toward a friction locking engagement with strap 20. The inner handle assembly is disengaged from this configuration and pulled into a second configuration wherein there is no interference of strap 20 when an operator grasps the handle and overcomes the spring bias. The operator can then slide the chafe when it is in a low friction configuration and when the desired adjustment has been made, a user can let go of the handle and the fiction locking mechanism of the inner handle returns to its default locking configuration.

FIG. 8F is a side view of chafe 50-S showing two-part of the handle 64 in down position, the two parts of the handle 64 in a separated position, and further showing the path of strap 20 through chafe 50-S. FIG. 8G is a side view of chafe 50-S showing two-part handle 64 in an elevated position, the two parts of the handle in a closed position, and further showing the path of strap 20 through the connector and the chafe.

The two parts of handle 64 (outer part 64-0 and inner part 64-I) can move between a separated configuration and locked (FIG. 8D) and a closed and unlocked configuration (FIG. 8E), as controlled by the state (uncompressed or compressed) of spring 65, which itself, is controlled by a user manipulating the two parts of handle 64.

The configuration shown in FIG. 8D wherein the two parts of the handle are separated, is a default state locked state of chafe 50-S. In this configuration, handle gap 67 is open, and handle strap gap 68 is minimal. The minimal opening of strap gap 68 maximizes frictional resistance of strap 20 through the gap, thereby forming a friction lock mechanism. FIG. 8D also shows a boss feature 64-Q that is built into the outer handle as a counterforce surface on each side for compression spring 65 within the inner handle.

FIG. 8E (in contrast to FIG. 8D) shows a configuration wherein the two parts of the handle are closed. This is an active, user-driven, unlocked state, one that results from a user squeezing the two parts of the handle together. In this state, handle gap 67 is closed, and handle strap gap 68 is open. The maximal opening of strap gap 68 minimizes frictional resistance of strap 20 through the gap, thereby unlocking the default locked state (as in FIG. 8D). FIG. 8E also shows that the square pin 64-H has slid into slot 64-G and spring 65 has compressed while the inner handle has also slide relative to boss feature 64-Q of the outer handle.

FIGS. 8F and 8G (as in FIGS. 8D and 8E) show chafe 50-S in an unlocked state and a locked state, respectively, and further show the path of strap 20 through chafe 50-S, and the role of the end 64-E of inner handle 64-I in locking and unlocking the chafe Additionally, FIG. 8D shows two part handle 64 in a down position, and FIG. 8E shows two part handle 64 in an elevated position.

The locked state of chafe 50-S (FIG. 8F) is evident by handle gap 67 being open and strap gap 68 being closed, thereby creating a friction lock at the nexus of the inner end 68 (of inner handle 64-I) and central bar 54-S of chafe 50S, with strap 20 trapped therebetween. The unlocked state of chafe 50-S (FIG. 8G) is evident by handle gap 67 being closed and strap gap 68 being open, thereby allowing strap 20 to move through the strap gap freely (or with minimal friction).

Although FIG. 8F shows handle 64 of chafe 50S in a down position and shows chafe 50S in locked configuration and FIG. 8G shows handle 64 of chafe 50S in an elevated position and shows chafe 50S in an unlocked configuration, the locked-unlocked status of the chafe is independent of the state of elevation (down or elevated).

FIGS. 9A-9E show views of an embodiment of an adjustable closure device 101-CH having a hinged handle 60-CH having base 54-CH configured as an integrated cam, the cam of the handle being positioned proximate the central bar 54-CH of a chafe 50-CH, the cam of the handle base and the central bar being collectively configured to act as friction-based strap lock. The "CH" designation refers the base of the handle being configured as a cam. Inasmuch as FIGS. 9A-9E show only a single chafe 50-CH, these figures can represent also an aspect of a bilateral adjustable closure device 102-CH.

Figure 9A:
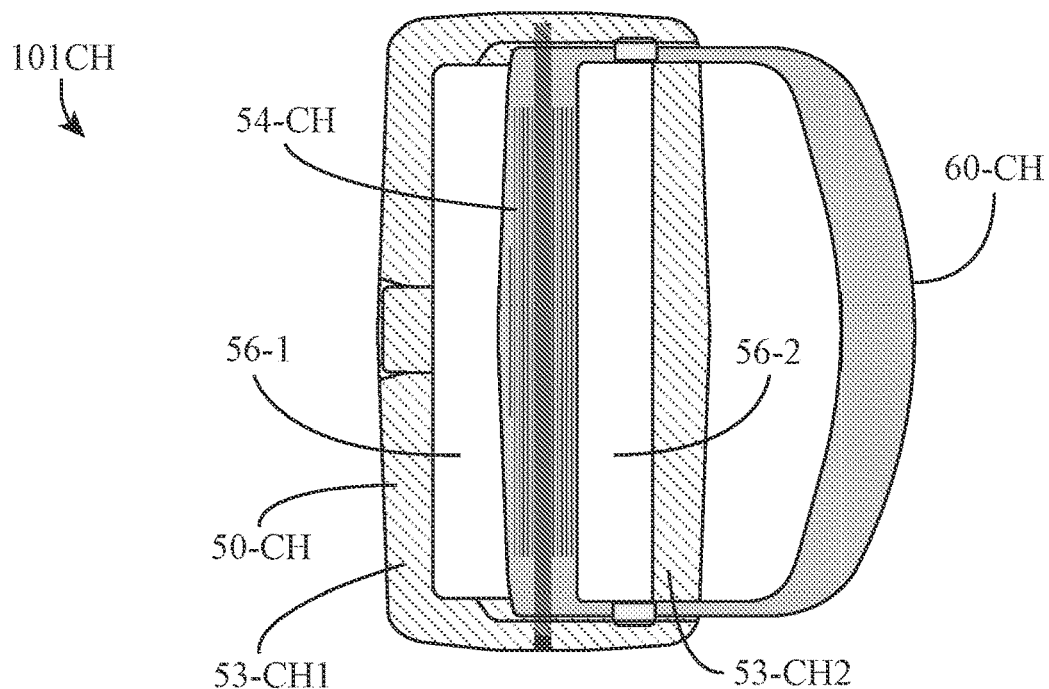
FIGS. 9A-9E show views of an embodiment of an adjustable closure device having a handle with an integrated cam positioned within the handle base, the cam proximate the central bar of a chafe, the cam configured to act as friction-based strap lock.

FIG. 9A is a face view of a chafe 50-CH and hinged handle 60-CH of an embodiment of an adjustable closure device 101-CH having a handle with a base 60-BC configured as an integrated cam that is positioned proximate the central bar 54-CH of a chafe, wherein handle base 60-BC and central bar 54-CH are collectively configured to act as friction-based strap lock.

Figure 9B:
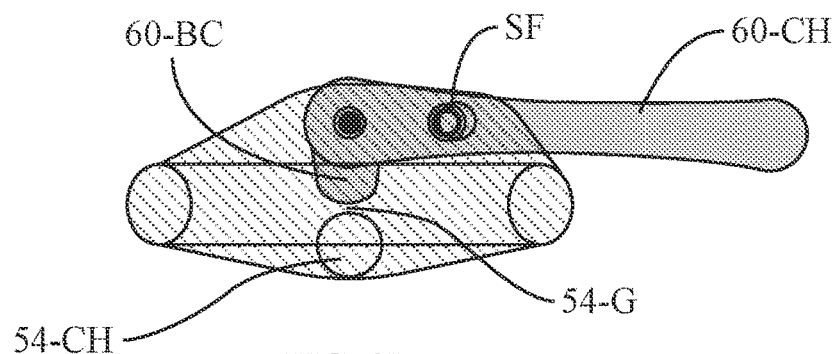
Figure 9C:
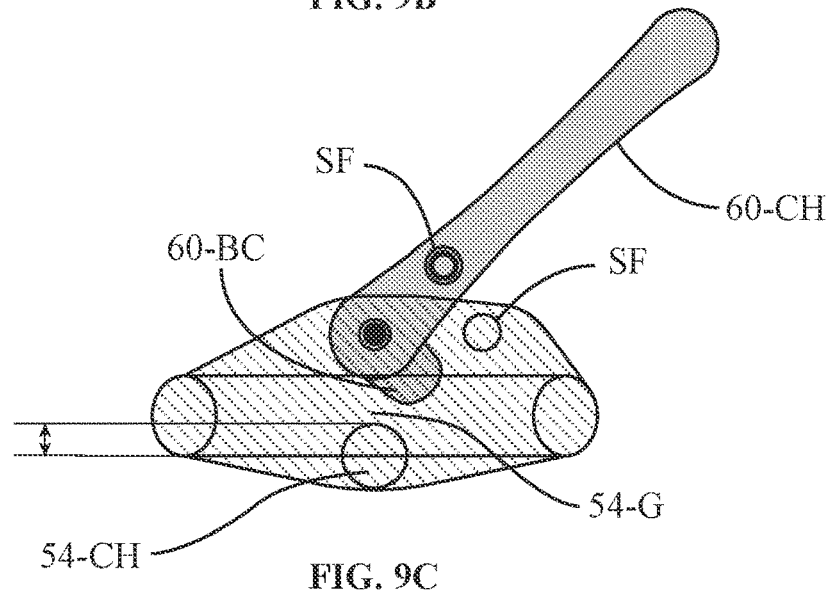

FIG. 9B is a side view of a chafe 50-CH and hinged handle 60-CH of FIG. 9A, with the handle in a down position. FIG. 9C is a side view of chafe 50-CH and hinged handle 60-CH of FIG. 9A, with hinged handle 60-CH in an elevated position.

Figure 9D:
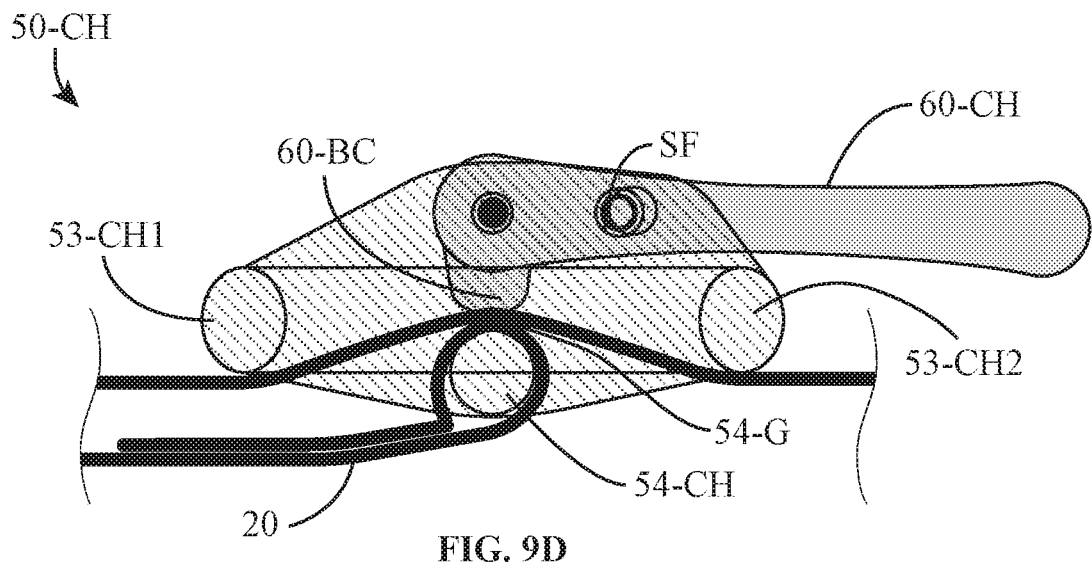
Figure 9E:
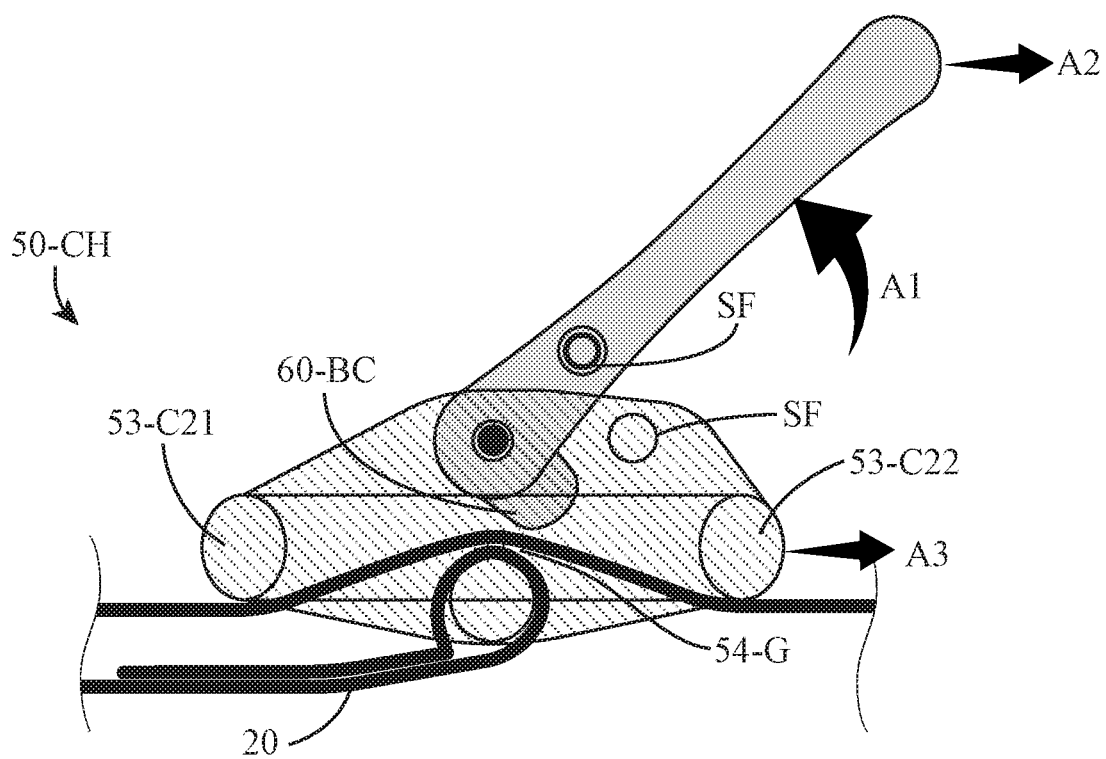

FIG. 9D is a side view of a chafe 50-CH and hinged handle 60-CH with the handle in a down position (as in FIG. 9B), but further showing the path of a strap 20 through the chafe. FIG. 9E is a side view of chafe 50-CH and hinged handle 60-CH with the handle in an elevated position (as in FIG. 9C), but further showing the path of a strap 20 through the chafe.

When handle 60-CH is in a down position (FIG. 9D), its position is stabilized or retained by a retention mechanism, exemplified here by a pair mateable of snap-fit components SF that are disposed on apposing sides of handle 60-CH and chafe 50-CH.

FIGS. 9D and 9E show the cooperation of cam base 60-BC and central bar 54-CH in creating a friction lock mechanism that can either allow or disallow movement of strap 20 through chafe 50-CH. FIG. 9D shows chafe 50-CH in a locked position. With handle 60-CH in a down position, cam 60-BC of the handle and central bar 54-CH of chafe 50-CH meet at a nexus that applies pressure to strap 20 as it passes through an adjustable gap 54G.

FIG. 9E shows chafe 50-CH in a locked position. With handle 60-CH in an elevated position, cam 60-BC of the handle and central bar 54-CH of chafe 50-CH are spaced apart such that strap 20 as it passes through an adjustable gap 54G with minimal friction between the cam base of the handle and the central bar. Arrow A1 shows directionality of handle 60-CH elevating; arrow A2 shows the direction of a manual pull that is allowed when handle 60-CH is in the elevated position; arrow A3 shows the direction that chafe 50-CH moves along strap 20, when the handle is elevated (A1) and being pulled (A2). A manual pull, per arrow A2, pulls chafe 50-CH along strap 20, away from the connector and closer to the central region of strap 20.

Accordingly, these cooperating aspects of handle 60-CH (including its rotatability and its cam base) and central bar 54 of chafe 50-CH, collectively form a friction locking mechanism that controls movement of strap 20 through the chafe, the rotation of handle 60-CH being under the control of a user. Further, by a user manipulating handle 60-CH (per arrows A1, A2, and A3), the user can move adjustable closure device 101-CH between a large circumference configuration and a small circumference configuration.

Figure 10A:
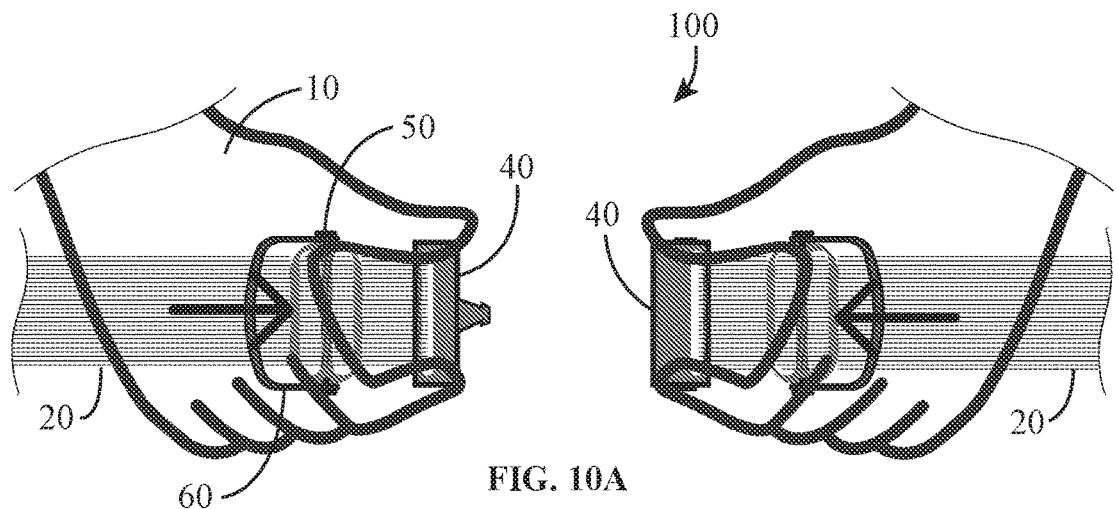
FIGS. 10A-10C show views of a method of connecting the connectors of an embodiment of a closure device, engaging the handles of the chafes, and drawing the handles apart to tighten the straps.
Figure 10B:
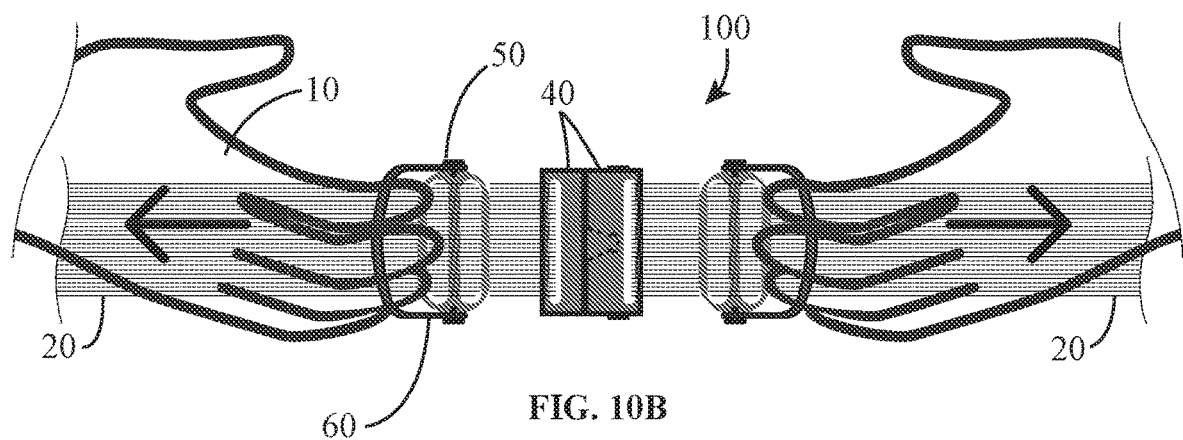
Figure 10C:
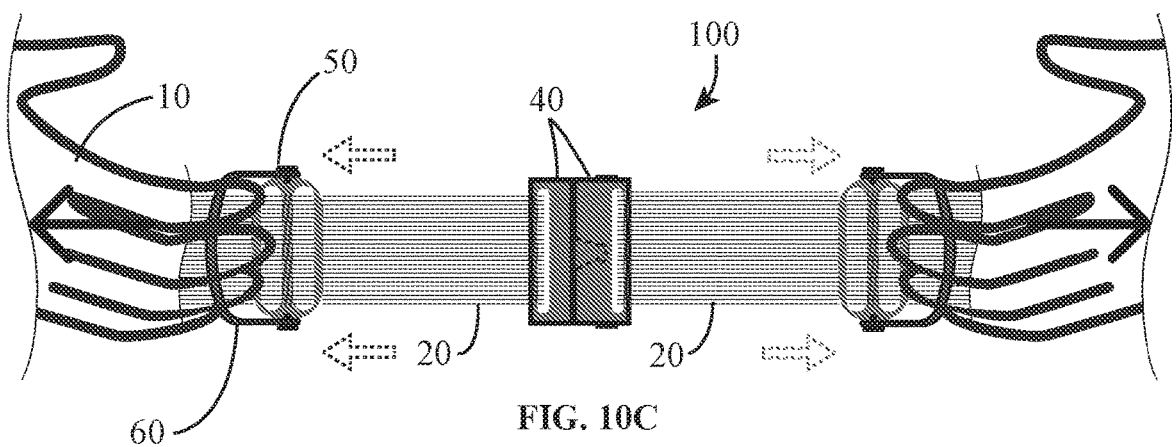

FIGS. 10A-10C show views of a method of connecting the connectors of an embodiment of an adjustable closure device 100 (broadly representing all embodiments of an adjustable closure device provided herein) engaging the handles 60 of chafes 50, and drawing the handles apart to tighten straps 20. FIG. 10A shows the hands of a user 10 engaging the two connectors 40 of the two ends of a strap 20, and preparing to connect them. FIG. 10B shows hands of a user 10 engaging handles 60 of chafes 50, and elevating them, preparing to draw the chafes apart. FIG. 10C shows the hands of a user 10 having now pulled chafes 50 apart, and tightening the two ends strap 20.

Adjustable closure device 100, chafe 50, handles 60 of the chafes, connectors 40, and strap 20 are all intended to generically represent all embodiments of adjustable closure devices and their component parts, as described, and as depicted herein. The depicted embodiment of adjustable device 100 shows a bilaterally adjustable closure device, but applies to a unilaterally adjustable closure device as well, with the modification of the user grasping a non-adjustable strap or an article to which the adjustable strap is connected.

FIGS. 11A-11M show various applications of embodiments of an adjustable closure device 100 as applied to various products.

Figure 11A:
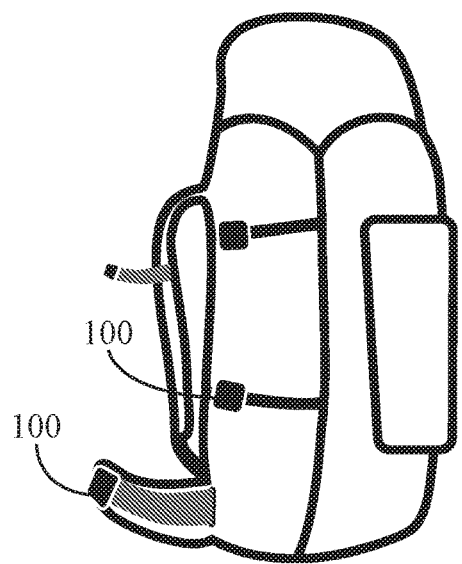
FIGS. 11A-11M show various applications of an adjustable closure device to products.

FIG. 11A shows application of an embodiment of an adjustable closure device 100 to a full sized backpack.

Figure 11B:
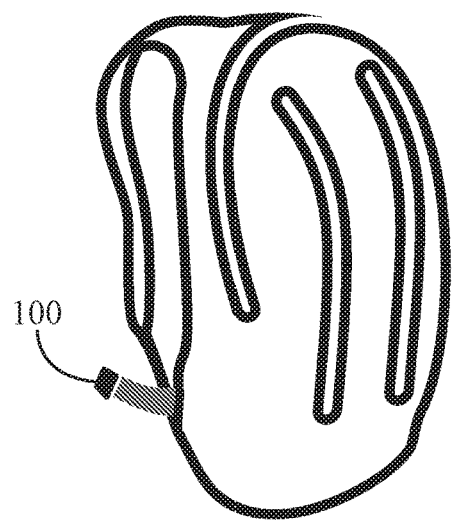

FIG. 11B shows application of an embodiment of an adjustable closure device 100 to a day backpack.

Figure 11C:
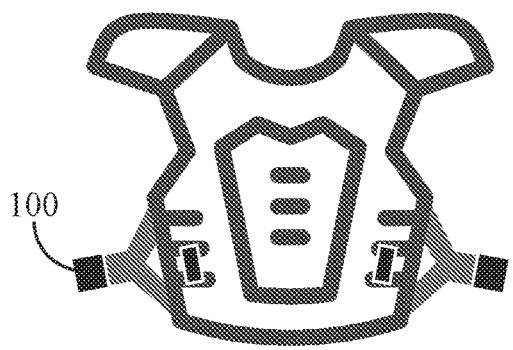

FIG. 11C shows application of an embodiment of an adjustable closure device 100 to a protective vest.

Figure 11D:
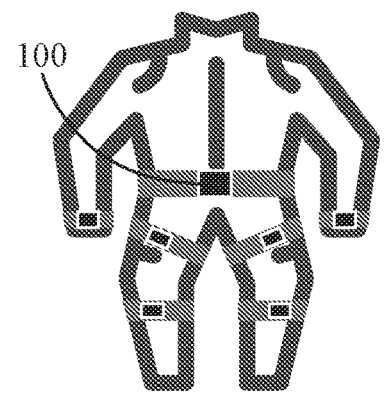

FIG. 11D shows application of an embodiment of an adjustable closure device 100 to motorcycle full body suit.

Figure 11E:
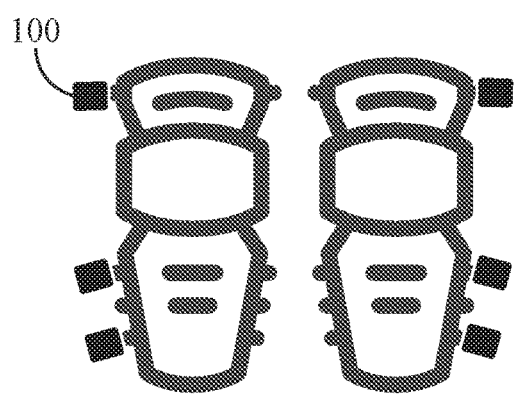

FIG. 11E shows application of an embodiment of an adjustable closure device 100 to protective knee pads.

Figure 11F:
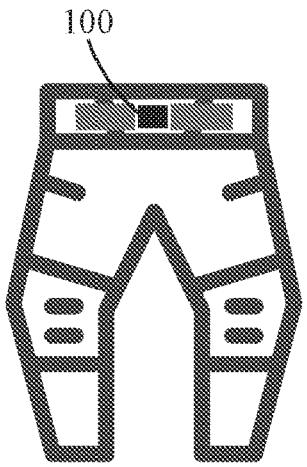

FIG. 11F shows application of an embodiment of an adjustable closure device 100 to a pair of protective pants.

Figure 11G:
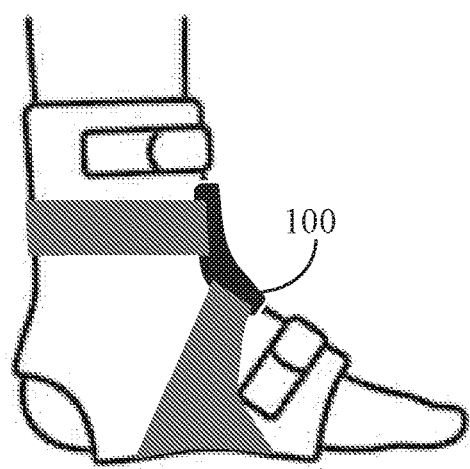

FIG. 11G shows application of an embodiment of an adjustable closure device 100 to an ankle brace.

Figure 11I:
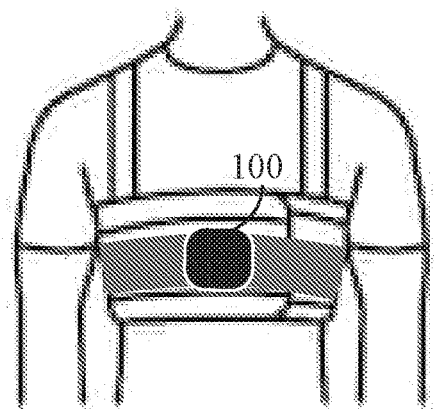
Figure 11H:
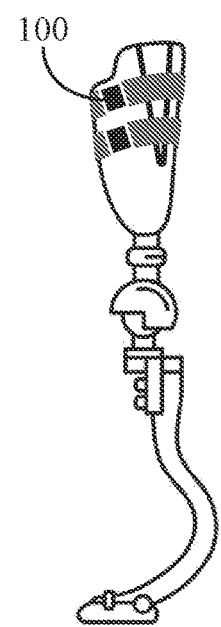

FIG. 11H shows application of an embodiment of an adjustable closure device 100 to a prosthetic socket.

FIG. 11I shows application of an embodiment of an adjustable closure device 100 to a back brace.

Figure 11J:
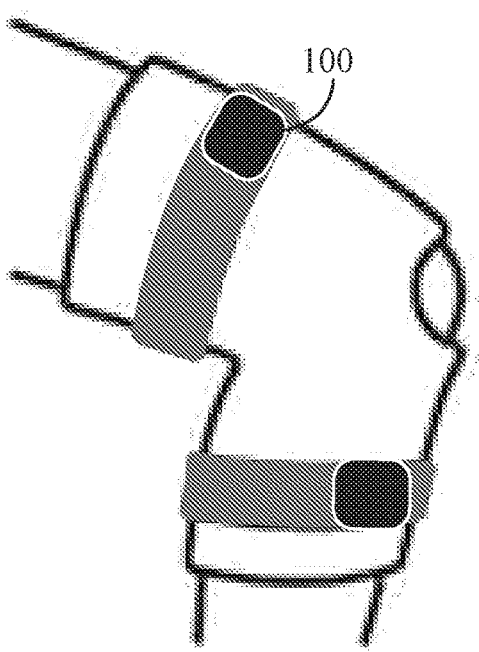

FIG. 11J shows application of an embodiment of an adjustable closure device 100 to a knee brace.

Figure 11K:
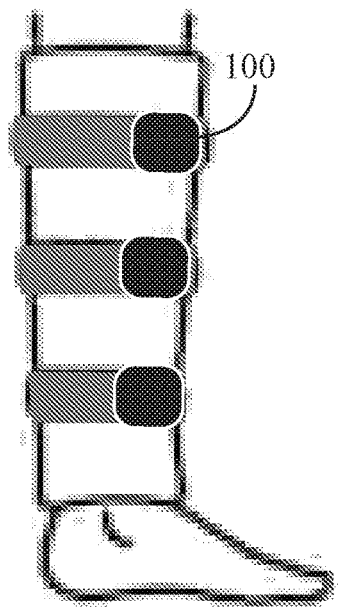

FIG. 11K shows application of an embodiment of an adjustable closure device 100 to a post-operative leg brace.

Figure 11L:
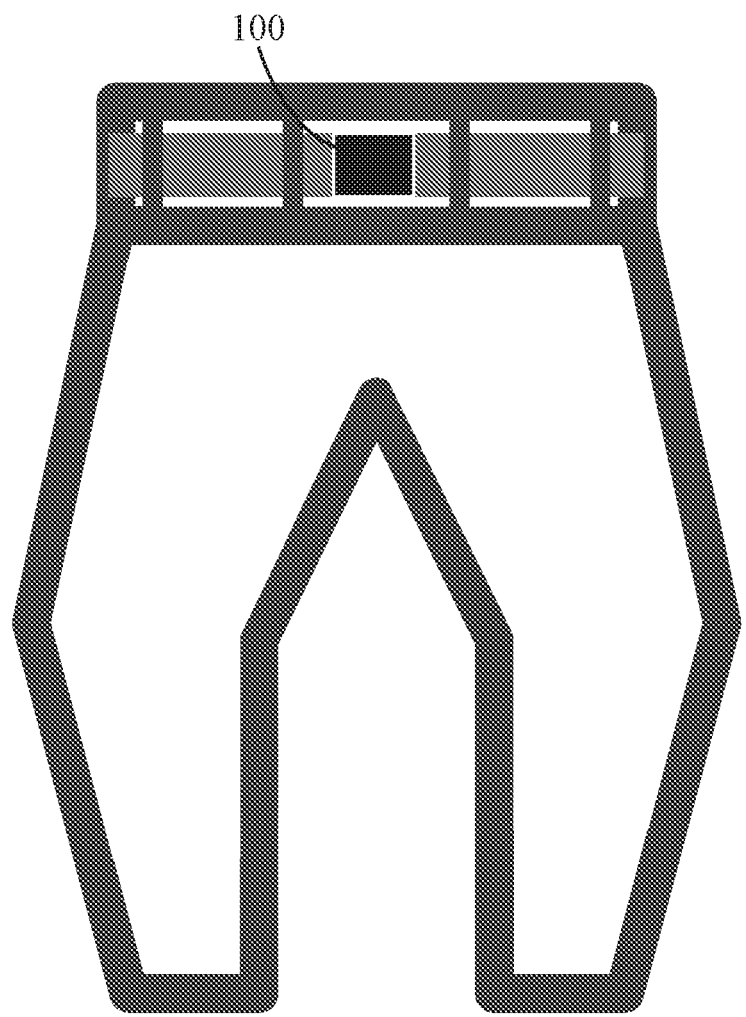

FIG. 11L shows application of an embodiment of an adjustable closure device 100 as a built-in belt for a pair of pants.

Figure 11M:
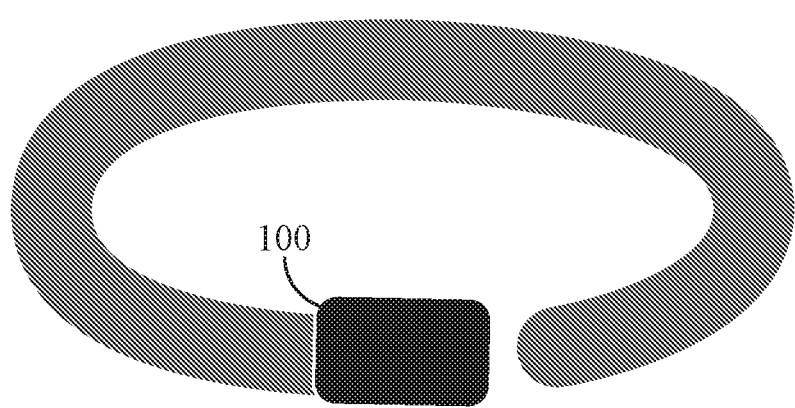

FIG. 11M shows application of an embodiment of an adjustable closure device 100 as a belt for a pair of pants.

Embodiment List

Multiple embodiments of an adjustable closure device, as disclosed herein, are listed below. This is a non-limiting list. The scope of provided invention includes embodiments in which any feature described or depicted in the context of any one embodiment can be appropriately combined with another embodiment.

A Unilaterally-Adjustable Closure Device

1. An adjustable closure device comprising:
a strap comprising at least a first end-region, and a central region;
a connector attached to a terminus of the at least first strap end-region wherein the connector comprises a strap pivot bar around which the strap reverses direction;
a chafe on the strap behind connector, the chafe comprising: three parallel bars, a first outer bar, a central bar, and a second outer bar, wherein the first outer bar is proximate the first end-region of the strap, the second outer bar is proximate the central-region of the strap, and wherein a first strap pass-through gap is disposed between the central bar and the first outer bar, and a second strap pass-through gap is disposed between the central bar and second outer bar; and wherein the strap end-region comprises a strap path comprising segments arranged, directionally from the strap's central region toward a strap terminus at the pivot bar of connector, to (a) pass through the first chafe gap, (b) pass by the central bar of the chafe, (c) through the second chafe gap, (d) around a strap pivot bar of connector, (e) return toward chafe and to loop around the central bar of the chafe and terminate thereto, and
wherein an adjustable length region of the strap comprises an adjustable span between the chafe's central bar and the connector attached to it; and
a handle connected to the chafe, wherein the handle is ergonomically configured to allow a user to pull the chafe to which it is connected along the strap, away from connector, and
wherein, when the chafe is allowed to move with respect to the strap, the strap can move between two configurations, wherein, by comparison, a first configuration comprises a large strap circumference and a second configuration comprises a small strap circumference.

2. The adjustable closure device of embodiment 1, wherein the central region of the strap is continuous with a second end region of the strap.

3. The adjustable closure device of embodiment 1, wherein the central region of the strap is wherein the central region of the strap is attached to an article.

4. The adjustable closure device of embodiment 1, wherein the connector is attached to the terminus of the first region is mateable with a second connector attached to a second terminus of the strap.

5. The adjustable closure device of embodiment 4, wherein the connector at the terminus of the first region is mateable with a second connector attached to a second terminus of the strap.

6. The adjustable closure device of embodiment 5, wherein the second connector attached to the second terminus of the strap comprises a second adjustable length region.

7. The adjustable closure device of embodiment 5, wherein second connector attached to a separate article.

8. The adjustable closure device of embodiment 1 wherein the chafe comprises a connector-side and a central-side, and wherein the handle is connected to the chafe at a mounting site proximate the central bar of the chafe, and wherein the mounting site comprises a handle hinge.

9. The adjustable closure device of embodiment 8 wherein the handle of each chafe can rotate at the hinge between a down position and an elevated position, wherein the elevated position elevates the handle on a central side of the chafe.

10. The adjustable closure device of embodiment 9 wherein the chafe comprises a handle-down retention mechanism.

11. The adjustable closure device of embodiment 1 wherein each chafe comprises a strap friction-based locking mechanism, which, when locked, disallows strap slippage through the chafe, and which, when unlocked, allows strap slippage through the chafe.

12. The chafe of embodiment 11, wherein the adjustable length region of the strap comprises two overlapping sections of the strap, a first section proximate the central region of the strap and a second section proximate the connector, and wherein the strap friction-based locking mechanism is positioned to engage on the adjustable length region of the strap.

13. The adjustable closure device of embodiment 1 wherein the strap friction-locking mechanism comprises a configuration wherein a base of the handle and the central bar of the chafe are integrated together, and wherein the central bar is configured as a one-sided cam.

14. The adjustable closure device of embodiment 13 wherein strap friction-locking mechanism comprises a configuration wherein the handle and the central bar of the chafe are integrated together, and wherein the central bar is configured as a one-sided cam.

15. The adjustable closure device of embodiment 14 wherein when the one-sided cam is rotated such that the cam has a maximal peak height over the side bars of the chafe, the chafe is in a locked position, and wherein when the one-sided cam is rotated such that the one side cam does not rise over a minimal circumference of the central bar, the chafe is in an unlocked position.

16. The adjustable closure device of embodiment 1 wherein the strap friction-locking mechanism comprises a configuration wherein a base of the handle and the central bar of the chafe are integrated together, and wherein the central bar is configured as a two-sided cam.

17. The adjustable closure device of embodiment 16 wherein the strap friction-locking mechanism comprises a configuration wherein the handle and the central bar of the chafe are integrated together, and wherein the central bar is configured as a two-sided cam.

18. The adjustable closure device of embodiment 17 wherein when the two-sided cam is rotated such that the cam has a maximal peak height over the side bars of the chafe, the chafe is in a locked position, and wherein when the two-sided cam is rotated such that the two-sided cam does not rise over a minimal circumference of the central bar, the chafe is in an unlocked position.

19. The adjustable closure device of embodiment 1 wherein the chafe handle comprises two parts, an outer handle and an inner handle, wherein the inner handle is nested within the outer handle and connected by a hinge thereto, wherein the inner handle and the outer handle are adjustable with respect to each other between the unlocked configuration and the locked configuration, and wherein the unlocked configuration is stabilized by a spring between the inner and outer handle that is uncompressed, and wherein the locked configuration is one wherein the spring is compressed.

20. The adjustable closure device of embodiment 1 wherein the handle comprises a cam-configured base that is proximate the central bar of the chafe but separated therefrom by a strap gap through which the strap passes, and wherein when the handle is in a down position the cam aspect of the base minimizes the strap gap, forming a locked configuration, and wherein when the handle is in an elevated position the cam aspect of the base maximizes the strap gap, forming an unlocked configuration.

A Bilaterally-Adjustable Closure Device

21. An adjustable closure device comprising:
a strap comprising a first end-region, a central region, and a second end-region;
two mutually connectable connectors, a first connector and second connector, wherein each connector is attached is to a terminus of one of the strap end-regions wherein each connector comprises a strap pivot bar around which the strap reverses direction;
two chafes, each chafe mounted on the strap behind the proximate connector, each chafe comprising:
three parallel bars, a first outer bar, a central bar, and a second outer bar, wherein the first outer bar is proximate the first end-region of the strap, the second outer bar is proximate the central-region of the strap, and wherein a first strap pass-through gap is disposed between the central bar and the first outer bar, and a second strap pass-through gap is disposed between the central bar and second outer bar; and
wherein each strap end-region comprises a strap path comprising segments arranged, directionally from the strap's central region toward a strap terminus at the pivot bar of connector, to (a) pass through the first chafe gap, (b) pass by the central bar of the chafe, (c) through the second chafe gap, (d) around a pulley pivot of connector, (e) return toward chafe and to loop around the central bar of the chafe and terminate thereto, and wherein an adjustable length region of the strap comprises an adjustable span between the chafe's central bar and the connector attached to it; and
a handle connected to each chafe, wherein the handle is ergonomically configured to allow a user to pull the chafe to which it is connected along the strap, away from connector, and
wherein, when each chafe is allowed to move with respect to the strap, the strap can move between two configurations, wherein, by comparison, a first configuration comprises a large strap circumference and a second configuration comprises a small strap circumference.

22. The adjustable closure device of embodiment 1 wherein each chafe comprises a connector-side and a central-side, and wherein the handle of each chafe is connected to the chafe at a mounting site proximate the central bar of the chafe, and wherein the mounting site comprises a handle hinge.

23. The adjustable closure device of embodiment 22 wherein the handle of each chafe can rotate at the hinge between a down position and an elevated position, wherein the elevated position elevates the handle on the central side of the chafe.

24. The adjustable closure device of embodiment 23 wherein each chafe comprises a handle-down retention mechanism.

25. The adjustable closure device of embodiment 1 wherein each chafe comprises a strap friction-based locking mechanism, which, when locked, disallows strap slippage through the chafe, and which, when unlocked, allows strap slippage through the chafe.

26. The chafe of embodiment 25, wherein the adjustable length region of each strap comprises two overlapping sections of the strap, a first section proximate the central region of the strap and a second section proximate the connector, and wherein the strap friction-based locking mechanism is positioned to engage on the adjustable length region of the strap.

27. The adjustable closure device of embodiment 1 wherein the strap friction-locking mechanism comprises a configuration wherein a base of the handle and the central bar of each chafe are integrated together, and wherein the central bar is configured as a one-sided cam.

28. The adjustable closure device of embodiment 27 wherein when the one-sided cam is rotated such that the cam has a maximal peak height over the side bars of the chafe, the chafe is in a locked position, and wherein when the one-sided cam is rotated such that the one side cam does not rise over a minimal circumference of the central bar, the chafe is in an unlocked position.

29. The adjustable closure device of embodiment 1 wherein the strap friction-locking mechanism comprises a configuration wherein a base of the handle and the central bar of each chafe are integrated together, and wherein the central bar is configured as a two-sided cam.

30. The adjustable closure device of embodiment 29 wherein strap friction-locking mechanism comprises a configuration wherein the handle and the central bar of the chafe are integrated together, and wherein the central bar is configured as a two-sided cam.

31. The adjustable closure device of embodiment 30 wherein when the two-sided cam is rotated such that the cam has a maximal peak height over the side bars of the chafe, the chafe is in a locked position, and wherein when the two-sided cam is rotated such that the two-sided cam does not rise over a minimal circumference of the central bar, the chafe is in an unlocked position.

32. The adjustable closure device of embodiment 1 wherein each chafe handle comprises two parts, an outer handle and an inner handle, wherein the inner handle is nested within the outer handle and connected by a hinge thereto, wherein the inner handle and the outer handle are adjustable with respect to each other between the unlocked configuration and the locked configuration, and wherein the unlocked configuration is stabilized by a spring between the inner and outer handle that is uncompressed, and wherein the locked configuration is one wherein the spring is compressed.

33. The adjustable closure device of embodiment 1 wherein each handle comprises a cam-configured base that is proximate the central bar of the chafe but separated therefrom by a strap gap through which the strap passes, and wherein when the handle is in a down position the cam aspect of the base minimizes the strap gap, forming a locked configuration, and wherein when the handle is in an elevated position the cam aspect of the base maximizes the strap gap, forming an unlocked configuration.

A Unilaterally-Adjustable Closure Device with a Pulley Arrangement

34. An adjustable closure device comprising:
   a strap comprising a first end-region, and a central region;
   a connectable connector, wherein the connector is attached to a terminus of the strap end-region, and wherein the connector comprises a first strap pivot bar and a second pivot bar, internal to the first strap pivot bar;
   a chafe mounted at the end of at the strap end-region, the chafe comprising:
      three parallel bars, a first outer bar, a central bar, and a second outer bar, wherein the first outer bar is proximate the first end-region of the strap, the second outer bar is proximate the central-region of the strap, and wherein a first strap pass-through gap is disposed between the central bar and the first outer bar, and a second strap pass-through gap is disposed between the central bar and second outer bar; and
   wherein the strap end-region comprises a strap path comprising segments arranged, directionally from the strap's central region and toward the strap terminus, to (a) pass through the first chafe gap, (b) pass by the central chafe bar, (c) pass through the second chafe gap, (d) pass toward the connector, to loop around the second pivot bar and reversing direction, (e) returning toward the chafe to pass around the central bar of the chafe and reversing direction, and finally (f) returning toward the connector, to loop around the first pivot bar of the connector and there to terminate, and
   wherein an adjustable length region of the strap comprises an adjustable span between the chafe and the connector; and
   a handle connected to the chafe, wherein the handle is ergonomically configured to allow a user to pull each chafe along the strap, away from the connector, and wherein, when the chafe is allowed to move with respect to the strap and wherein the strap can move between two configurations, wherein, by comparison, a first configuration comprises a large strap circumference and a second configuration comprises a small strap circumference.

35. The adjustable closure device of embodiment 34 wherein the strap path comprises a pulley arrangement in which the strap reverses direction twice, thereby providing mechanical advantage upon pulling the chafe with respect to the strap, wherein the force required to shorten the adjustable length region of strap is less than that which would be required absent the pulley arrangement to move the device from the first configuration to the second configuration.

36. The adjustable closure device of embodiment 35, wherein the mechanical advantage is about 2:1.

37. The adjustable closure device of embodiment 35, wherein the central region of the strap is continuous with a second end region of the strap.

38. The adjustable closure device of embodiment 35, wherein the connector is mateable with a second connector attached to a second terminus of the strap.

39. The adjustable closure device of embodiment 38, wherein the strap attached to the second terminus of the strap comprises a second adjustable length region.

40. The adjustable closure device of embodiment 38, wherein second connector attached to a separate article.

41. The adjustable closure device of embodiment 35, wherein the central region of the strap is attached to an article.

42. The adjustable closure device of embodiment 34 wherein the chafe comprises a connector-side and a central-side, and wherein the handle is connected to the chafe at a mounting site proximate the central bar of the chafe, and wherein the mounting site comprises a hinge supporting the handle.

43. The adjustable closure device of embodiment 42 wherein the handle of the chafe can rotate at the hinge between a down position and an elevated position, wherein the elevated position elevates the handle on the central side of the chafe.

44. The adjustable closure device of embodiment 43 wherein the chafe comprises a handle-down retention mechanism.

45. The adjustable closure device of embodiment 34 wherein each chafe comprises a strap friction-locking mechanism, which, when in a locked position, disallows strap slippage through the chafe, and which, when in an unlocked position, allows strap slippage through the chafe.

46. The chafe of embodiment 45, wherein the adjustable length region of the strap comprises two overlapping sections of the strap, a first section proximate the central region of the strap and a second section proximate the connector, and wherein the strap friction-based locking mechanism is positioned to engage on the adjustable length region of the strap.

47. The adjustable closure device of embodiment 34 wherein the strap friction-locking mechanism comprises a configuration wherein a base of the handle and the central bar of the chafe are integrated together, and wherein the central bar is configured as a one-sided cam.

48. The adjustable closure device of embodiment 47 wherein when the one-sided cam is rotated such that the cam has a maximal peak height over the side bars of the chafe, the chafe is in a locked position, and wherein when the one-sided cam is rotated such that the one side cam does not rise over a minimal circumference of the central bar, the chafe is in an unlocked position.

49. The adjustable closure device of embodiment 34 wherein the strap friction-locking mechanism comprises a configuration wherein a base of the handle and the central bar of the chafe are integrated together, and wherein the central bar is configured as a two-sided cam.

50. The adjustable closure device of embodiment 49 wherein when the two-sided cam is rotated such that the cam has a maximal peak height over the side bars of the chafe, the chafe is in a locked position, and wherein when the two-sided cam is rotated such that the two-sided cam does not rise over a minimal circumference of the central bar, the chafe is in an unlocked position.

51. The adjustable closure device of embodiment 34 wherein the chafe handle comprises two parts, an outer handle and an inner handle, wherein the inner handle is nested within the outer handle and connected by a hinge thereto, wherein the inner handle and the outer handle are adjustable with respect to each other such that the two handle parts can be spaced apart or aligned together, wherein when the two handle parts are spaced apart, the chafe is in a locked position, and when two handle parts are aligned together, the chafe is in an unlocked position.

52. The adjustable closure device of embodiment 51 further comprising a spring that when in an uncompressed state, maintains the first and second handle parts in the spaced apart configuration such that the chafe is in the unlocked position, and when the spring is in a compressed state, the first and second handle parts are aligned together, and the chafe is an the locked configuration.

53. The adjustable closure device of embodiment 34 wherein the handle comprises a cam-configured base that is proximate the central bar of the chafe but separated therefrom by a strap gap through which the strap path passes.

54. The adjustable closure device of embodiment 53 wherein when the handle is in a down position the cam aspect of the base minimizes the strap gap, forming a locked configuration, and wherein when the handle is in an elevated position, the cam aspect of the base maximizes the strap gap, forming an unlocked configuration.

A Bilaterally-Adjustable Closure Device with a Pulley Arrangement

55. An adjustable closure device comprising:
   a strap comprising a first end-region, a central region, and a second end-region;
   two mutually connectable connectors, a first connector and second connector, wherein each connector is attached is to a terminus of one of the strap end-regions wherein each connector comprises a first strap pivot bar and second pivot bar, internal to the first strap pivot bar;
   two chafes, one mounted at the end of at each strap end-region, each chafe comprising: three parallel bars, a first outer bar, a central bar, and a second outer bar, wherein the first outer bar is proximate the first end-region of the strap, the second outer bar is proximate the central-region of the strap, and wherein a first strap pass-through gap is disposed between the central bar and the first outer bar, and a second strap pass-through gap is disposed between the central bar and second outer bar; and
   wherein each strap end-region comprises a strap path comprising segments arranged, directionally from the strap's central region and toward the strap terminus, to (a) pass through the first chafe gap, (b) pass by the central chafe bar, (c) pass through the second chafe gap, (d) pass toward the connector, to loop around the second pivot bar and reversing direction, (e) returning toward the chafe to pass around the central bar of the chafe and reversing direction, and finally (f) returning toward the connector, to loop around the first pivot bar of the connector and terminate thereto, and
   wherein an adjustable length region of the strap comprises an adjustable span between the each of the two chafes, the two chafes connected by the connectors; and
   a handle connected to each chafe, wherein the handle is ergonomically configured to allow a user to pull each chafe along the strap, away from the first connector, and
   wherein, when each chafe is allowed to move with respect to the strap and wherein the strap can move between two configurations, wherein, by comparison, a first configuration comprises a large strap circumference and a second configuration comprises a small strap circumference.

56. The adjustable closure device of embodiment 55 wherein the strap path comprises a pulley arrangement in which the strap reverses direction twice, thereby providing mechanical advantage upon pulling the chafe with respect to the strap, wherein the force required to shorten the adjustable length region of strap is less than that which would be required absent the pulley arrangement to move the device from the first configuration to the second configuration.

57. The adjustable closure device of embodiment 56, wherein the mechanical advantage is about 2:1.

58. The adjustable closure device of embodiment 55 wherein each chafe comprises a connector-side and a central-side, and wherein the handle is connected to the chafe at a mounting site proximate the central bar of the chafe, and wherein the mounting site comprises a hinge supporting the handle.

59. The adjustable closure device of embodiment 58 wherein the handle of the chafe can rotate at the hinge between a down position and an elevated position, wherein the elevated position elevates the handle on the central side of the chafe.

60. The adjustable closure device of embodiment 59 wherein the chafe comprises a handle-down retention mechanism.

61. The adjustable closure device of embodiment 55 wherein each chafe comprises a strap friction-locking mechanism, which, when in a locked position, disallows strap slippage through the chafe, and which, when in an unlocked position, allows strap slippage through the chafe.

62. The chafe of embodiment 61, wherein the adjustable length region of the strap comprises two overlapping sections of the strap, a first section proximate the central region of the strap and a second section proximate the connector, and wherein the strap friction-based locking mechanism is positioned to engage on the adjustable length region of the strap.

63. The adjustable closure device of embodiment 61 wherein the strap friction-locking mechanism comprises a configuration wherein a base of the handle and the central bar of the chafe are integrated together, and wherein the central bar is configured as a one-sided cam.

64. The adjustable closure device of embodiment 63 wherein when the one-sided cam is rotated such that the cam has a maximal peak height over the side bars of the chafe, the chafe is in a locked position, and wherein when the one-sided cam is rotated such that the one side cam does not rise over a minimal circumference of the central bar, the chafe is in an unlocked position.

65. The adjustable closure device of embodiment 61 wherein the strap friction-locking mechanism comprises a configuration wherein a base of the handle and the central bar of the chafe are integrated together, and wherein the central bar is configured as a two-sided cam.

66. The adjustable closure device of embodiment 65 wherein when the two-sided cam is rotated such that the cam has a maximal peak height over the side bars of the chafe, the chafe is in a locked position, and wherein when the two-sided cam is rotated such that the two-sided cam does not rise over a minimal circumference of the central bar, the chafe is in an unlocked position.

67. The adjustable closure device of embodiment 61 wherein each chafe handle comprises two parts, an outer handle and an inner handle, wherein the inner handle is nested within the outer handle and connected by a hinge thereto, wherein the inner handle and the outer handle are adjustable with respect to each other such that the two handle parts can be spaced apart or aligned together, wherein when the two handle parts are spaced apart, the chafe is in a locked position, and when two handle parts are aligned together, the chafe is in an unlocked position.

68. The adjustable closure device of embodiment 67 further comprising a spring that when in an uncompressed state, maintains the first and second handle parts in the spaced apart configuration such that the chafe is in the unlocked position, and when the spring is in a compressed state, the first and second handle parts are aligned together, and the chafe is an the locked configuration.

69. The adjustable closure device of embodiment 61 wherein each handle comprises a cam-configured base that is proximate the central bar of the chafe but separated therefrom by a strap gap through which the strap path passes.

70. The adjustable closure device of embodiment 69 wherein when the handle is in a down position the cam aspect of the base minimizes the strap gap, forming a locked configuration, and wherein when the handle is in an elevated position, the cam aspect of the base maximizes the strap gap, forming an unlocked configuration.

The invention claimed is:

1. An adjustable closure device comprising:
a strap comprising a first end-region, and a central region;
a connectable connector, wherein the connector is attached to a terminus of the strap end-region, and wherein the connector comprises a first strap pivot bar and a second pivot bar, internal to the first strap pivot bar;
a chafe mounted at the end of the strap end-region, the chafe comprising:
three parallel bars, a first outer bar, a central bar, and a second outer bar, wherein the first outer bar is proximate the first end-region of the strap, the second outer bar is proximate the central-region of the strap, and wherein a first strap pass-through gap is disposed between the central bar and the first outer bar, and a second strap pass-through gap is disposed between the central bar and second outer bar; and
wherein the strap end-region comprises a strap path comprising segments arranged, directionally from the strap's central region and toward the strap terminus, to (a) pass through the first chafe gap, (b) pass by the central chafe bar, (c) pass through the second chafe gap, (d) pass toward the connector, to loop around the second pivot bar and reversing direction, (e) returning toward the chafe to pass around the central bar of the chafe and reversing direction, and finally (f) returning toward the connector, to loop around the first pivot bar of the connector and there to terminate, and
wherein an adjustable length region of the strap comprises an adjustable span between the chafe and the connector; and
a handle connected to the chafe, wherein the handle is ergonomically configured to allow a user to pull the chafe along the strap, away from the connector, and
wherein, when the chafe is allowed to move with respect to the strap and wherein the strap can move between two configurations, wherein, by comparison, a first configuration comprises a large strap circumference and a second configuration comprises a small strap circumference.

2. The adjustable closure device of claim 1 wherein the strap path comprises a pulley arrangement in which the strap reverses direction twice, thereby providing mechanical advantage upon pulling the chafe with respect to the strap, wherein the force required to shorten the adjustable length region of strap is less than that which would be required absent the pulley arrangement to move the device from the first configuration to the second configuration.

3. The adjustable closure device of claim 2, wherein the mechanical advantage is about 2:1.

4. The adjustable closure device of claim 2, wherein the central region of the strap is continuous with a second end region of the strap.

5. The adjustable closure device of claim 2, wherein the connector is mateable with a second connector attached to a second terminus of the strap.

6. The adjustable closure device of claim 5, wherein the strap attached to the second terminus of the strap comprises a second adjustable length region.

7. The adjustable closure device of claim 5, wherein the second connector is attached to a separate article.

8. The adjustable closure device of claim 2, wherein the central region of the strap is attached to an article.

9. The adjustable closure device of claim 1 wherein the chafe comprises a connector-side and a central-side, and wherein the handle is connected to the chafe at a mounting site proximate the central bar of the chafe, and wherein the mounting site comprises a hinge supporting the handle.

10. The adjustable closure device of claim 9 wherein the handle of the chafe can rotate at the hinge between a down position and an elevated position, wherein the elevated position elevates the handle on the central side of the chafe.

11. The adjustable closure device of claim 10 wherein the chafe comprises a handle-down retention mechanism.

12. The adjustable closure device of claim 1 wherein the chafe comprises a strap friction-locking mechanism, which, when in a locked position, disallows strap slippage through the chafe, and which, when in an unlocked position, allows strap slippage through the chafe.

13. The chafe of claim 12, wherein the adjustable length region of the strap comprises two overlapping sections of the strap, a first section proximate the central region of the strap and a second section proximate the connector, and wherein the strap friction-locking mechanism is positioned to engage on the adjustable length region of the strap.

14. The adjustable closure device of claim 12 wherein the strap friction-locking mechanism comprises a configuration wherein a base of the handle and the central bar of the chafe are integrated together, and wherein the central bar is configured as a one-sided cam.

15. The adjustable closure device of claim 14 wherein when the one-sided cam is rotated such that the cam has a maximal peak height over the side bars of the chafe, the chafe is in a locked position, and wherein when the one-sided cam is rotated such that the one side cam does not rise over a minimal circumference of the central bar, the chafe is in an unlocked position.

16. The adjustable closure device of claim 12 wherein the strap friction-locking mechanism comprises a configuration wherein a base of the handle and the central bar of the chafe are integrated together, and wherein the central bar is configured as a two-sided cam.

17. The adjustable closure device of claim 16 wherein when the two-sided cam is rotated such that the cam has a maximal peak height over the side bars of the chafe, the chafe is in a locked position, and wherein when the two-sided cam is rotated such that the two-sided cam does not rise over a minimal circumference of the central bar, the chafe is in an unlocked position.

18. The adjustable closure device of claim 12 wherein the chafe handle comprises two parts, an outer handle and an inner handle, wherein the inner handle is nested within the outer handle and connected by a hinge thereto, wherein the inner handle and the outer handle are adjustable with respect to each other such that the two handle parts can be spaced apart or aligned together, wherein when the two handle parts are spaced apart, the chafe is in a locked position, and when the two handle parts are aligned together, the chafe is in an unlocked position.

19. The adjustable closure device of claim 18 further comprising a spring that when in an uncompressed state, maintains the first and second handle parts in the spaced apart configuration such that the chafe is in the unlocked position, and when the spring is in a compressed state, the first and second handle parts are aligned together, and the chafe is in the locked configuration.

20. The adjustable closure device of claim 12 wherein the handle comprises a cam-configured base that is proximate the central bar of the chafe but separated therefrom by a strap gap through which the strap path passes.

21. The adjustable closure device of claim 20 wherein when the handle is in a down position the cam-configured base minimizes the strap gap, forming a locked configuration, and wherein when the handle is in an elevated position, the cam-configured base maximizes the strap gap, forming an unlocked configuration.

22. An adjustable closure device comprising:
  a strap comprising a first end-region, a central region, and a second end-region;
  two mutually connectable connectors, a first connector and second connector, wherein each connector is attached is to a terminus of one of the strap end-regions wherein each connector comprises a first strap pivot bar and second pivot bar, internal to the first strap pivot bar;
  two chafes, one mounted at the end of each strap end-region, each chafe comprising:
    three parallel bars, a first outer bar, a central bar, and a second outer bar, wherein the first outer bar is proximate the first end-region of the strap, the second outer bar is proximate the central-region of the strap, and wherein a first strap pass-through gap is disposed between the central bar and the first outer bar, and a second strap pass-through gap is disposed between the central bar and second outer bar; and
  wherein each strap end-region comprises a strap path comprising segments arranged, directionally from the strap's central region and toward the strap terminus, to (a) pass through the first chafe gap, (b) pass by the central chafe bar, (c) pass through the second chafe gap, (d) pass toward the connector, to loop around the second pivot bar and reversing direction, (e) returning toward the chafe to pass around the central bar of the chafe and reversing direction, and finally (f) returning toward the connector, to loop around the first pivot bar of the connector and terminate thereto, and
  wherein an adjustable length region of the strap comprises an adjustable span between each of the two chafes, the two chafes connected by the connectors; and
  a handle connected to each chafe, wherein the handle is ergonomically configured to allow a user to pull each chafe along the strap, away from the first connector, and
  wherein, when each chafe is allowed to move with respect to the strap and wherein the strap can move between two configurations, wherein, by comparison, a first configuration comprises a large strap circumference and a second configuration comprises a small strap circumference.

23. The adjustable closure device of claim 22 wherein the strap path comprises a pulley arrangement in which the strap reverses direction twice, thereby providing a mechanical advantage upon pulling the chafes with respect to the strap, in terms of the force required to shorten the adjustable length region, thereby moving from the first configuration to the second configuration.

24. The adjustable closure device of claim 23, wherein the mechanical advantage is about 2:1.

* * * * *